United States Patent
Shen et al.

(10) Patent No.: US 9,796,732 B2
(45) Date of Patent: Oct. 24, 2017

(54) PYRIDOPYRIMIDINE OR PYRIMIDOPYRIMIDINE COMPOUND, PREPRATION METHOD, PHARMACEUTICAL COMPOSITION, AND USE THEREOF

(71) Applicants: Shanghai Institute of Materia Medica, Chinese Academy of Sciences, Shanghai (CN); Fudan University, Shanghai (CN)

(72) Inventors: Jingkang Shen, Shanghai (CN); Ke Yu, Shanghai (CN); Tao Meng, Shanghai (CN); Lanping Ma, Shanghai (CN); Arie Zask, Shanghai (CN); Lanfang Meng, Shanghai (CN); Xin Wang, Shanghai (CN); Yiyi Chen, Shanghai (CN)

(73) Assignee: SHANDONG LUOXIN PHARMACEUTICAL GROUP STOCK CO., LTD., Linyi (CN)

( * ) Notice: Subject to any disclaimer, the term of this patent is extended or adjusted under 35 U.S.C. 154(b) by 0 days.

(21) Appl. No.: 14/842,682

(22) Filed: Sep. 1, 2015

(65) Prior Publication Data
US 2015/0368274 A1    Dec. 24, 2015

Related U.S. Application Data

(63) Continuation of application No. PCT/CN2014/072678, filed on Feb. 28, 2014.

(30) Foreign Application Priority Data

Mar. 4, 2013    (CN) .......................... 2013 1 0068888

(51) Int. Cl.
*A61K 31/519*    (2006.01)
*C07D 519/00*    (2006.01)
*C07D 471/04*    (2006.01)
*C07D 487/04*    (2006.01)

(52) U.S. Cl.
CPC ......... *C07D 519/00* (2013.01); *C07D 471/04* (2013.01); *C07D 487/04* (2013.01)

(58) Field of Classification Search
CPC .................................................. C07D 519/00
See application file for complete search history.

(56) References Cited

FOREIGN PATENT DOCUMENTS

| CN | 102887895 | 1/2013 |
|---|---|---|
| CN | 103588792 | 2/2014 |
| RU | 2448109 C2 | 4/2012 |
| WO | WO 2013/016999 | 2/2013 |

OTHER PUBLICATIONS

Lin et al. Mammalian target of rapamycin (mTOR) inhibitors in solid tumours. 2016, Clinical Pharmacist, vol. 8, No. 3, 1-23.*
International Search Report and Written Opinion for International Application No. PCT/CN2014/072678, mailed May 30, 2014, 16 pages (with English Translation).
Pike, K.G. et al., "Optimization of potent and selective dual mTORC1 and mTORC2 inhibitors: The discovery of AZD8055 and AZD2014," Bioorganic & Medicinal Chemistry Letters, 23(5):1212-1216 (Jan. 2013).
Supplementary European Search Report for European Application No. 14760712.1, dated Oct. 10, 2016, 9 pages.

* cited by examiner

*Primary Examiner* — Brian McDowell
(74) *Attorney, Agent, or Firm* — Cooley LLP

(57) ABSTRACT

The present invention belongs to the field of pharmaceutical Chemistry. In particular, the present invention relates to a pyridopyrimidine or pyrimidopyrimidine compound as represented by general formula (I), or an isomer thereof or a pharmaceutically acceptable salt, ester, prodrug or solvate thereof, a preparation method, a pharmaceutical composition and uses thereof in preparing a mTOR inhibitor. As a mTOR inhibitor, the compound or the pharmaceutical composition thereof can be used for treating a disease or condition due to PI3K-AKT-mTOR signalling pathway malfunction.

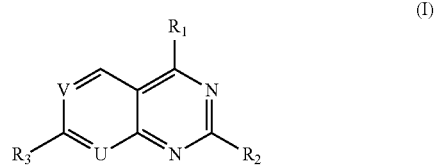

13 Claims, No Drawings

PYRIDOPYRIMIDINE OR PYRIMIDOPYRIMIDINE COMPOUND, PREPRATION METHOD, PHARMACEUTICAL COMPOSITION, AND USE THEREOF

This application is a continuation application of International Application No. PCT/CN2014/072678, filed on Feb. 28, 2014, which claims the priority to CN 201310068888.8, filed on Mar. 4, 2013, the contents of each of which are herein incorporated by reference in their entirety.

TECHNICAL FIELD

The present invention belongs to the field of pharmaceutical chemistry. Specifically, the present invention relates to a class of pyridopyrimidine or pyrimidopyrimidine compounds, the isomers, the pharmaceutically acceptable salts, esters, prodrugs or solvates thereof, preparation method therefor, the pharmaceutical composition comprising the same, and the use thereof in preparing a mTOR inhibitor. Such compound or the pharmaceutical composition thereof as the mTOR inhibitor can be used in treating a disease or condition caused by malfunction of PI3K-AKT-mTOR signalling pathways.

BACKGROUND

Research in recent years shows that PI3K-AKT-mTOR signalling pathways play a key role in the growth, proliferation, invasion and metastasis of tumor cells, and blocking of PI3K-AKT-mTOR signalling pathways in the cells can inhibit the proliferation of tumor cells, and even promote apoptosis of tumor cells. In various kinds of human tumors, some key proteins in PI3K-AKT-mTOR signalling pathways may be overly activated, due to mutation or amplification of encoding genes, for example, the mutation or amplification of the upstream receptor tyrosine kinase, the mutation or amplification of PIK3CA gene encoding p110α catalytic subunit in various tumor cells, over activation of Akt and PDK1, and general deletion in the negative regulator PTEN.

Mammalian target of rapamycin, mTOR, which is one of the most important substrates for Akt, is a non-classical serine/threonine protein kinase of the phosphatidylinositol 3-kinase-related kinase (PIKK) family. mTOR signalling pathway can regulate a large number of life processes by integrating the signals transmitting from nutrition molecules, the energy status and growth factors, and thus is a key pathway for regulating the growth and proliferation of cells. Abnormal activation of mTOR signalling pathways is a common character of occurrence and development of various tumors, thus it becomes a hot spot in the research and development of an antitumor inhibitor.

However, it has been found that there are at least two functional complexes, i.e., mTORC1 and mTORC2, which mediate both related and independent biological signaling. Clinically used Rapamycin drug, including Rapamycin and analogues thereof, binds to FKBP12-rapamycin binding domain (FRB) around mTORC1 catalytic site via allostery, to exert the effects of partial inhibition of mTOR protein. These compounds neither directly inhibit mTORC2, nor completely block all the signals mediated by mTORC1. Although the rapamycin drug has shown cercern clinical efficacy in some tumor spectra, but the action mode of such kind of drug can not reach full potential of the mTOR targeted anticancer drugs. Especially, in some major solid tumors, AKT hyperphosphorylation (activation) mediated by mTORC2 is vital for maintenance and development of the tumors, but mTORC2 can not be inhibited by Rapamycin drugs.

The development of ATP-competitive and specific small molecule inhibitors of mTOR provides the possibility for treating a variety of cancers. Compared with Rapamycin drugs, some ATP-competitive inhibitors reported recently have shown better inhibitory effect on the growth and survival, protein synthesis, biological energy metabolism of tumor cells. In animal studies, this kind of drug has a strong single-drug antitumor activity on MDA361 breast cancer, U87MG glioma, A549 and H1975 lung cancer, A498 and 786-O kidney cancer.

In summary, as mTOR signaling pathway is involved in a variety of tumor spectra, the development of a more effective mTOR inhibitor provides fresh thinking and a new strategy for a novel broad-spectrum anti-tumor drug. Recently, several mTOR inhibitors have been entered into the clinical research phase, which indicates that the ATP-competitive inhibitor of mTOR may be a new generation of anticancer drug to be used in clinic.

The present inventor has confirmed that the mTOR inhibitor is an ATP-competitive inhibitor, thus its mechanism of action is different from that of Rapamycin drugs. In addition, the present inventors obtained a class of novel pyridopyrimidine or pyrimidopyrimidine compounds by rational design and comprehensive consideration of the factors such as water solubility, metabolic stability and the like of the compounds, based on previously reported compounds. Such compounds show good mTOR inhibition activity at the encymic and cellular levels. After further optimization and screening, these compounds are expected to become readily prepared anticancer drugs with higher activity.

SUMMARY OF THE INVENTION

Technical Object

One object of present invention is to provide a pyridopyrimidine or pyrimidopyrimidine compound represented by formula (I), the isomer, the pharmaceutically acceptable salt, the ester, the prodrug or the solvate thereof.

Another object of present invention is to provide a method of preparing the compound.

Yet another object of present invention is to provide use of the pyridopyrimidine or pyrimidopyrimidine compound represented by formula (I), the isomer, the pharmaceutically acceptable salts, the ester, the prodrug or the solvate thereof as a mTOR inhibitor, and use in treating a disease or condition caused by dysfunction of PI3K-AKT-mTOR signaling pathway, especially a tumor disease.

Another object of present invention is to provide a pharmaceutical composition comprising one or more selected from the group consisting of the pyridopyrimidine or pyrimidopyrimidine compound represented by formula (I), the isomer, the pharmaceutically acceptable salt, the ester, the prodrugs or the solvate thereof.

Another object of present invention is to provide a method of treating a disease or condition, especially a tumor disease, caused by dysfunction of PI3K-AKT-mTOR signaling pathway.

Technical Solution

According to one aspect of present invention, provided is a pyridopyrimidine or pyrimidopyrimidine compound represented by formula (I), the isomer, the pharmaceutically acceptable salt, the ester, the prodrug or the solvate thereof:

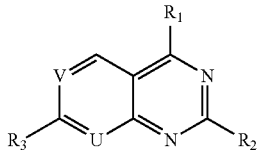

wherein, one of U and V is N, the other is CH, or both of U and V are N;

$R_1$ and $R_2$ are each independently 3-oxa-8-azabicyclo[3.2.1]octanyl, 8-oxa-3-azabicyclo[3.2.1]octanyl, or $NR_AR_B$, wherein, $R_A$ and $R_B$ are each independently H, C1-C6 alkyl unsubstituted or substituted by C1-C6 alkoxy or halogen, or C1-C6 alkoxy unsubstituted or substituted by halogen, or $R_A$ and $R_B$, together with N to which they linked, form a nitrogen-containing saturated heterocycle having 4 to 8 ring atoms, which is unsubstituted or substituted by C1-C6 alkyl, C1-C6 alkoxy or halogen, the nitrogen-containing saturated heterocycle includes piperidine ring, morpholine ring, piperazine ring, N-methyl piperazine ring, homomorpholine ring high, homopiperazine ring and the like, preferably, $R_1$ and $R_2$ are each independently 3-oxa-8-azabicyclo[3.2.1]octanyl, 8-oxa-3-azabicyclo[3.2.1]octanyl, or $NR_AR_B$, wherein, $R_A$ and $R_B$ are each independently H, C1-C3 alkyl unsubstituted or substituted by C1-C3 alkoxy or halogen, or C1-C3 alkoxy unsubstituted or substituted by halogen, or $R_A$ and $R_B$, together with N to which they linked, form a nitrogen-containing saturated heterocycle having 6 to 7 ring atoms which is unsubstituted or substituted by C1-C3 alkyl, C1-C3 alkoxy or halogen, the nitrogen-containing saturated heterocycle preferably is morpholine ring, more preferably, $R_1$ and $R_2$ are each independently

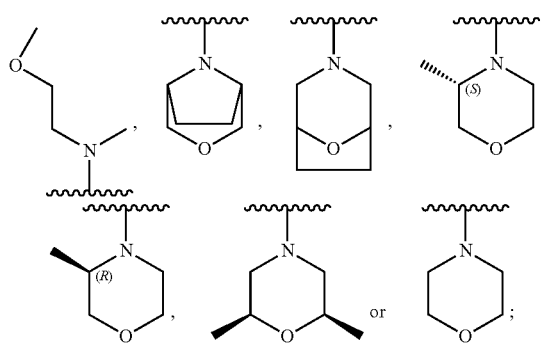

and $R_3$ is phenyl or pyridyl unsubstituted or substituted by 1 to 5 substituents, wherein the substituent may be halogen; hydroxyl; cyano; C1-C7 alkyl unsubstituted or substituted by C1-C7 alkoxy, halogen or hydroxy; C1-C7 alkoxy; —NHS(=O)$_2$C1-C7 alkyl; amino unsubstituted or substituted by C5-C6 aryl, C1-C7 alkyl or di(C1-C7 alkyl); —C(O)NH$_2$; or —C(O)NHC1-C3 alkyl, preferably, $R_3$ is phenyl unsubstituted or substituted by 1 to 3 substituents, wherein the substituent may behalogen; hydroxyl; cyano; C1-C4 alkyl unsubstituted or substituted by C1-C4 alkoxy, halogen or hydroxy; C1-C4 alkoxy; —NHS(=O)$_2$C1-C4 alkyl; amino unsubstituted or substituted by C5-C6 aryl, C1-C4 alkyl or di(C1-C4 alkyl); —C(O)NH$_2$; or —C(O)NHC1-C3 alkyl, more preferably, $R_3$ is

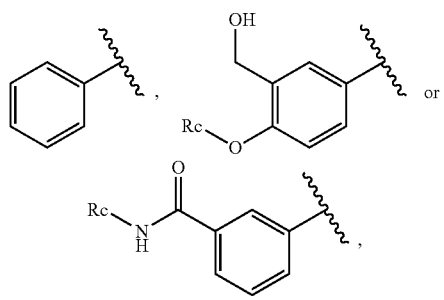

wherein, Rc is H or C1-C3 alkyl, preferably, Rc is H or methyl.

In the above formula (I), when U is N and V is CH, the compound represented by formula (I) is preferably the compound represented by formula (Ia):

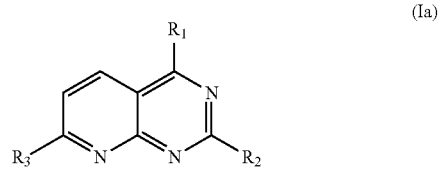

wherein, $R_1$ and $R_2$ are each independently 3-oxa-8-azabicyclo[3.2.1]octanyl, 8-oxa-3-azabicyclo[3.2.1]octanyl, or $NR_AR_B$, wherein, $R_A$ and $R_B$ are each independently H, C1-C6 alkyl unsubstituted or substituted by C1-C6 alkoxy or halogen, or C1-C6 alkoxy unsubstituted or substituted by halogen, or $R_A$ and $R_B$, together with N to which they linked, form a nitrogen-containing saturated heterocycle having 4 to 8 ring atoms which is unsubstituted or substituted by C1-C6 alkyl, C1-C6 alkoxy or halogen, the nitrogen-containing saturated heterocycle includes piperidine ring, morpholine ring, piperazine ring, N-methyl piperazine ring, homomorpholine ring high, homopiperazine ring and the like, preferably, $R_1$ and $R_2$ are each independently 3-oxa-8-azabicyclo[3.2.1]octanyl, 8-oxa-3-azabicyclo[3.2.1]octanyl, or $NR_AR_B$, wherein, $R_A$ and $R_B$ are each independently H, C1-C3 alkyl unsubstituted or substituted by C1-C3 alkoxy or halogen, or C1-C3 alkoxy unsubstituted or substituted by halogen, or $R_A$ and $R_B$, together with N to which they linked, form a nitrogen-containing saturated heterocycle having 6 to 7 ring atoms which is unsubstituted or substituted by C1-C3 alkyl, C1-C3 alkoxy or halogen, the nitrogen-containing saturated heterocycle preferably is morpholine ring, more preferably, $R_1$ and $R_2$ are each independently

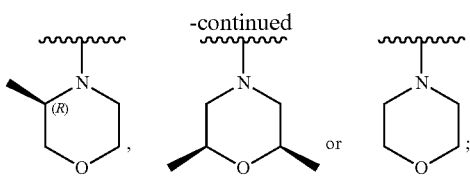

and

R₃ is phenyl or pyridyl unsubstituted or substituted by 1 to 5 substituents, wherein the substituent may be halogen; hydroxyl; cyano; C1-C7 alkyl unsubstituted or substituted by C1-C7 alkoxy, halogen or hydroxy; C1-C7 alkoxy; —NHS(=O)₂C1-C7 alkyl; amino unsubstituted or substituted by C5-C6 aryl, C1-C7 alkyl or di(C1-C7 alkyl); —C(O)NH₂; or —C(O)NH—C1-C3 alkyl, preferably, R₃ is phenyl unsubstituted or substituted by 1 to 3 substituents, wherein the substituent may be halogen; hydroxyl; cyano; C1-C4 alkyl unsubstituted or substituted by C1-C4 alkoxy, halogen or hydroxy; C1-C4 alkoxy; —NHS(=O)₂C1-C4 alkyl; amino unsubstituted or substituted by C5-C6 aryl, C1-C4 alkyl or di(C1-C4 alkyl); —C(O)NH₂; or —C(O)NHC1-C3 alkyl, more preferably, R₃ is

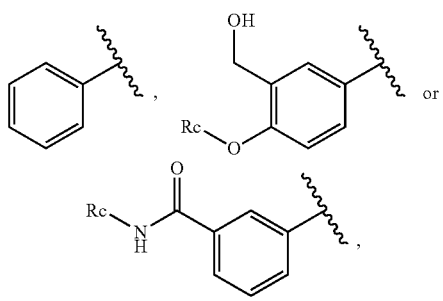

wherein, Rc is H or C1-C3 alkyl, preferably, Rc is H or methyl.

In the above formula (I), when U is CH, V is N, the compound represented by formula (I) is preferably the compound represented by formula (Ib):

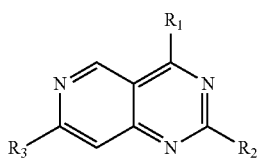

wherein,

R₁ and R₂ are each independently 3-oxa-8-azabicyclo[3.2.1]octanyl, 8-oxa-3-azabicyclo[3.2.1]octanyl, or NR$_A$R$_B$, wherein, R$_A$ and R$_B$ are each independently H, C1-C6 alkyl unsubstituted or substituted by C1-C6 alkoxy or halogen, or C1-C6 alkoxy unsubstituted or substituted by halogen, or R$_A$ and R$_B$, together with N to which they linked, form a nitrogen-containing saturated heterocycle having 4 to 8 ring atoms which is unsubstituted or substituted by C1-C6 alkyl, C1-C6 alkoxy or halogen, the nitrogen-containing saturated heterocycle includes piperidine ring, morpholine ring, piperazine ring, N-methyl piperazine ring, homomorpholine ring high, homopiperazine ring and the like, preferably, R₁ and R₂ are each independently 3-oxa-8-azabicyclo[3.2.1]octanyl, 8-oxa-3-azabicyclo[3.2.1]octanyl, or NR$_A$R$_B$, wherein, R$_A$ and R$_B$ are each independently H, C1-C3 alkyl unsubstituted or substituted by C1-C3 alkoxy or halogen, or C1-C3 alkoxy unsubstituted or substituted by halogen, or R$_A$ and R$_B$, together with N to which they linked, form a nitrogen-containing saturated heterocycle having 6 to 7 ring atoms, which is unsubstituted or substituted by C1-C3 alkyl, C1-C3 alkoxy or halogen, the nitrogen-containing saturated heterocycle preferably is morpholine ring, more preferably, R₁ and R₂ are each independently

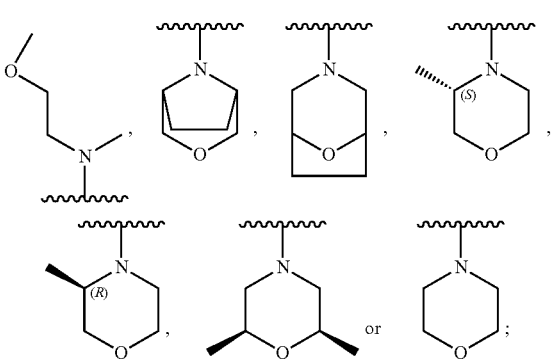

and

R₃ is phenyl or pyridyl unsubstituted or substituted by 1 to 5 substituents, wherein the substituent may be halogen; hydroxyl; cyano; C1-C7 alkyl unsubstituted or substituted by C1-C7 alkoxy, halogen or hydroxy; C1-C7 alkoxy; —NHS(=O)₂C1-C7 alkyl; amino unsubstituted or substituted by C5-C6 aryl, C1-C7 alkyl or di(C1-C7 alkyl); —C(O)NH₂; or —C(O)NH—C1-C3 alkyl, preferably, R₃ is phenyl unsubstituted or substituted by 1 to 3 substituents, wherein the substituent may be halogen; hydroxyl; cyano; C1-C4 alkyl unsubstituted or substituted by C1-C4 alkoxy, halogen or hydroxy; C1-C4 alkoxy; —NHS(=O)₂C1-C4 alkyl; amino unsubstituted or substituted by C5-C6 aryl, C1-C4 alkyl or di(C1-C4 alkyl); —C(O)NH₂; or —C(O)NHC1-C3 alkyl, more preferably, R3 is

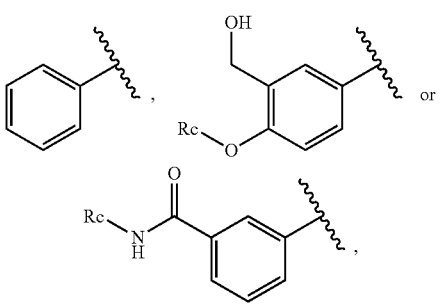

wherein, Rc is H or C1-C3 alkyl, preferably, Rc is H or methyl.

In the above formula (I), when both of U and V are N, the compound represented by formula (I) is preferably the compound represented by formula (Ic):

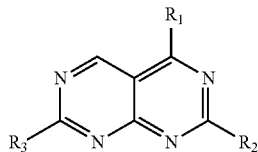

wherein,

R₁ and R₂ are each independently 3-oxa-8-azabicyclo[3.2.1]octanyl, 8-oxa-3-azabicyclo[3.2.1]octanyl, or NR$_A$R$_B$, wherein, R$_A$ and R$_B$ are each independently H, C1-C6 alkyl unsubstituted or substituted by C1-C6 alkoxy or halogen, or C1-C6 alkoxy unsubstituted or substituted by halogen, or R$_A$ and R$_B$, together with N to which they linked, form a nitrogen-containing saturated heterocycle having 4 to 8 ring atoms which is unsubstituted or substituted by C1-C6 alkyl, C1-C6 alkoxy or halogen, the nitrogen-containing saturated heterocycle includes piperidine ring, morpholine ring, piperazine ring, N-methyl piperazine ring, homomorpholine ring high, homopiperazine ring and the like, preferably, R₁ and R₂ are each independently 3-oxa-8-azabicyclo[3.2.1]octanyl, 8-oxa-3-azabicyclo[3.2.1]octanyl, or NR$_A$R$_B$, wherein, R$_A$ and R$_B$ are each independently H, C1-C3 alkyl unsubstituted or substituted by C1-C3 alkoxy or halogen, or C1-C3 alkoxy unsubstituted or substituted by halogen, or R$_A$ and R$_B$, together with N to which they linked, form a nitrogen-containing saturated heterocycle having 6 to 7 ring atoms which is unsubstituted or substituted by C1-C3 alkyl, C1-C3 alkoxy or halogen, the nitrogen-containing saturated heterocycle preferably is morpholine ring, more preferably, R₁ and R₂ are each independently

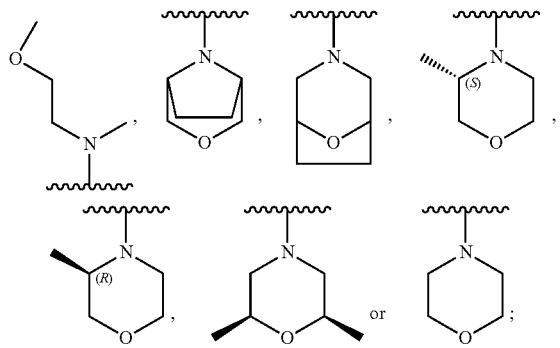

and

R₃ is phenyl or pyridyl unsubstituted or substituted by 1 to 5 substituents, wherein the substituent may be halogen; hydroxyl; cyano; C1-C7 alkyl unsubstituted or substituted by C1-C7 alkoxy, halogen or hydroxy; C1-C7 alkoxy; —NHS(=O)₂C1-C7 alkyl; amino unsubstituted or substituted by C5-C6 aryl, C1-C7 alkyl or di(C1-C7 alkyl); —C(O)NH₂; or —C(O)NH—C1-C3 alkyl, preferably, R₃ is phenyl unsubstituted or substituted by 1 to 3 substituents, wherein the substituent may be halogen; hydroxyl; cyano; C1-C4 alkyl unsubstituted or substituted by C1-C4 alkoxy, halogen or hydroxy; C1-C4 alkoxy; —NHS(=O)₂C1-C4 alkyl; amino unsubstituted or substituted by C5-C6 aryl, C1-C4 alkyl or di(C1-C4 alkyl); —C(O)NH₂; or —C(O)NHC1-C3 alkyl, more preferably, R3 is

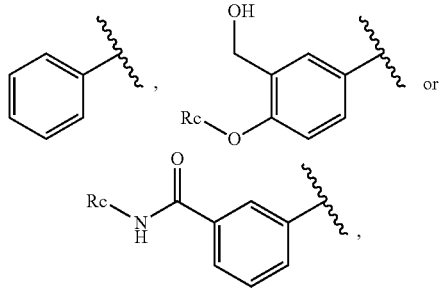

wherein, Rc is H or C1-C3 alkyl, preferably, Rc is H or methyl.

In present invention, particularly preferred specific compound is one of the following compounds:

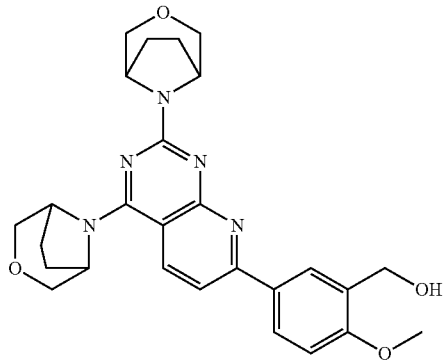

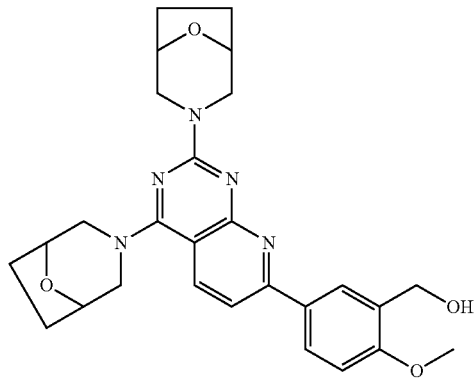

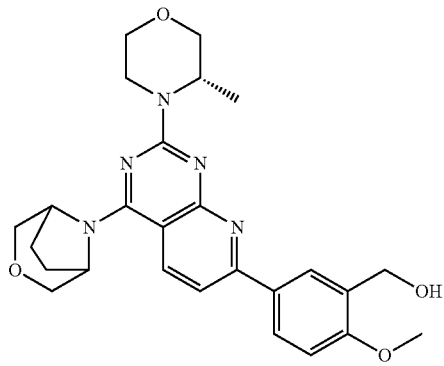

4
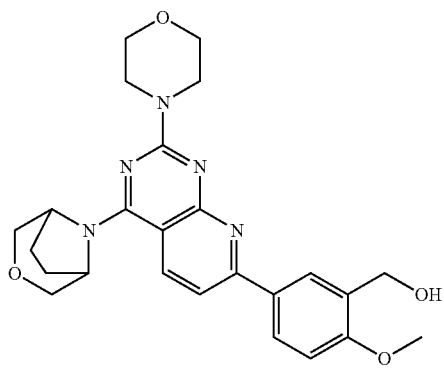
5
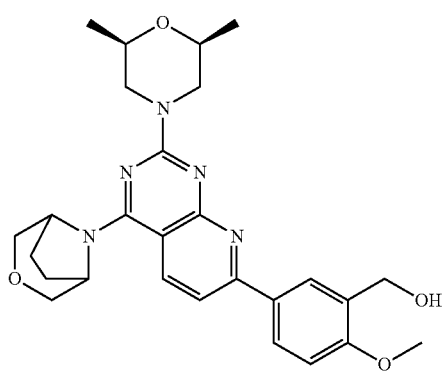
6
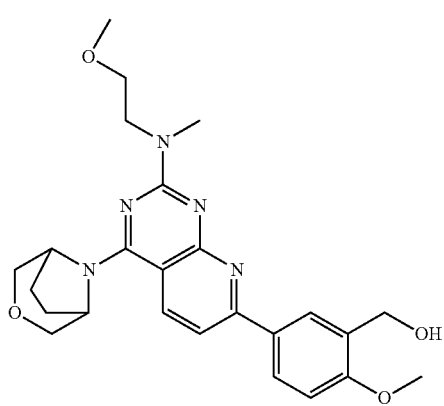
7
8
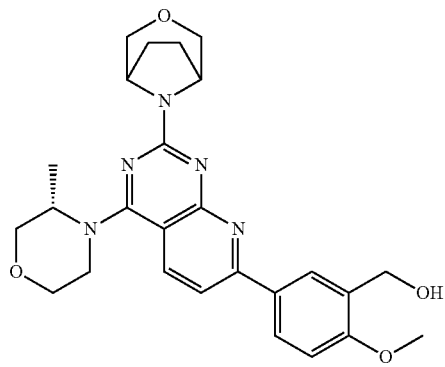
9
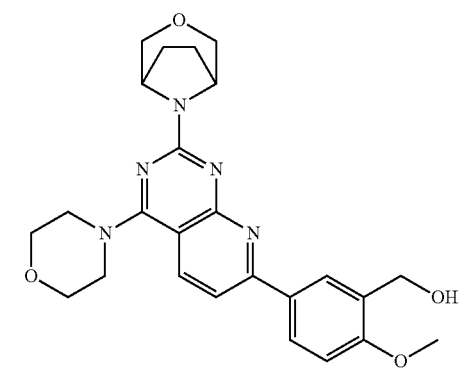
10
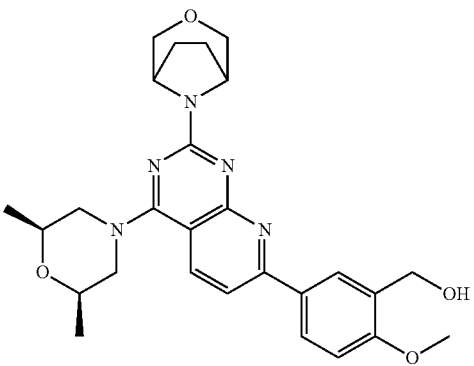
11
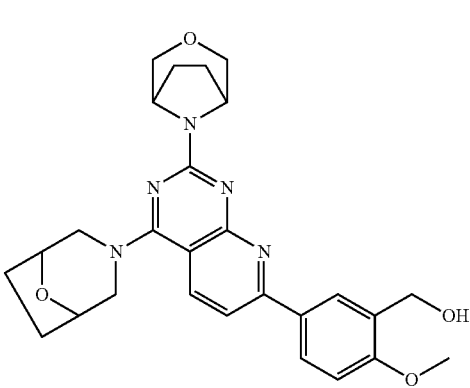

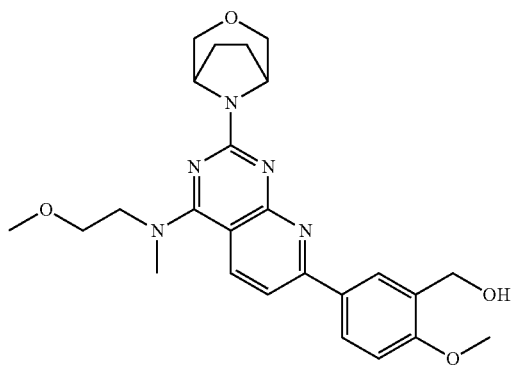
12
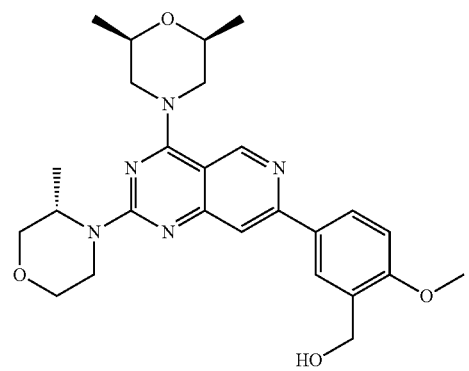
16
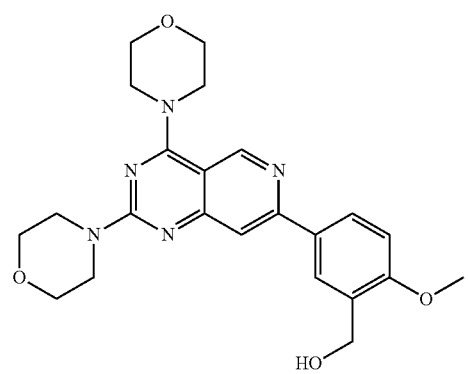
13
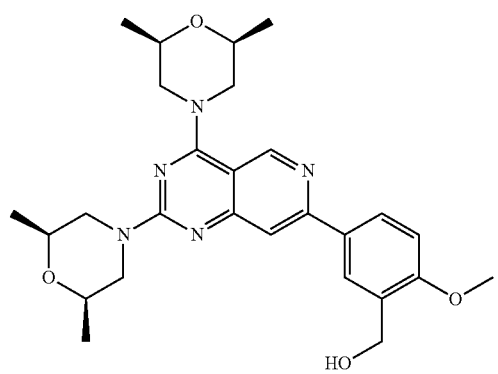
17
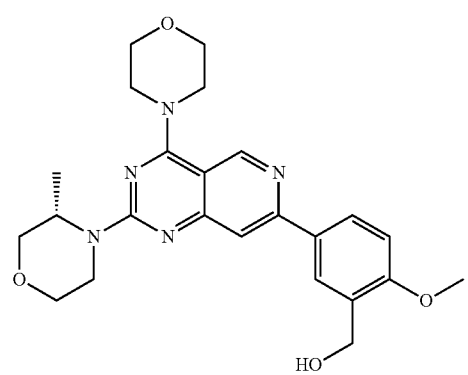
14
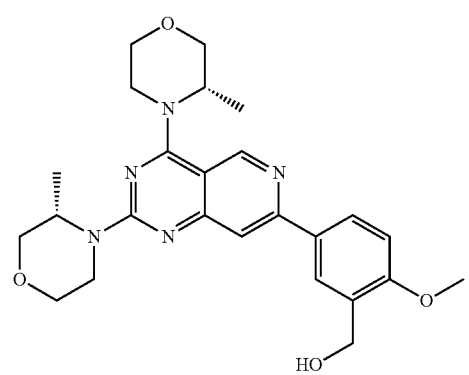
18
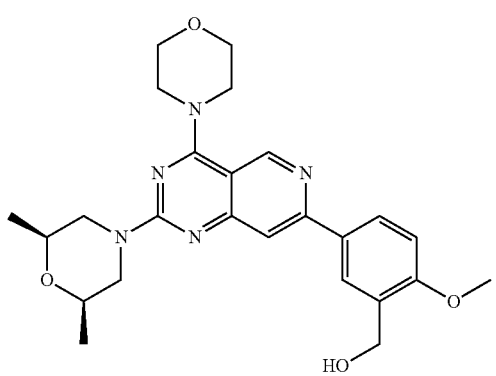
15
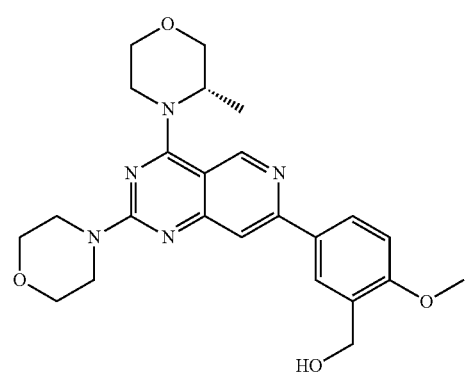
19

20
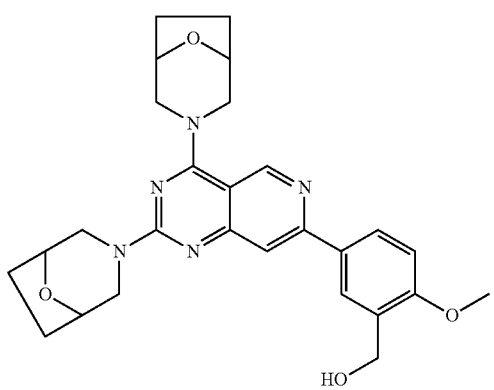
21
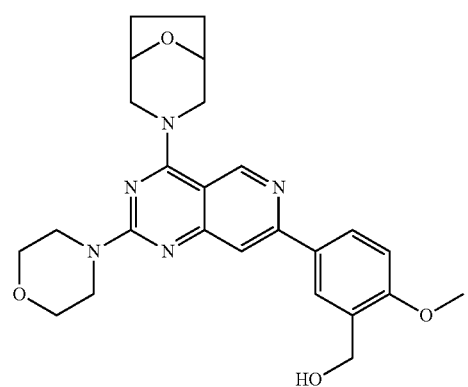
22
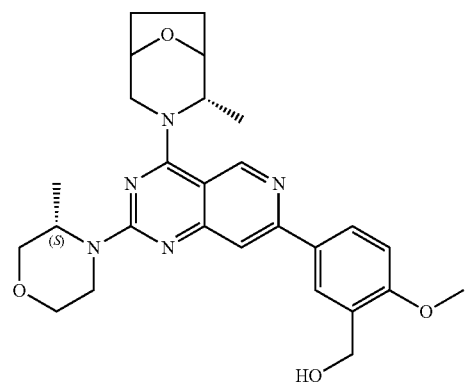
23
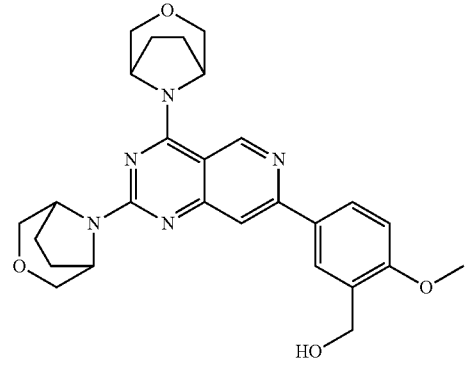
24
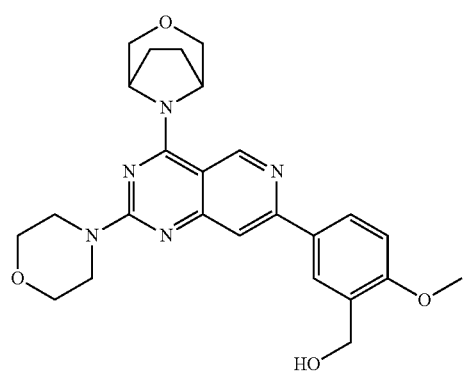
25
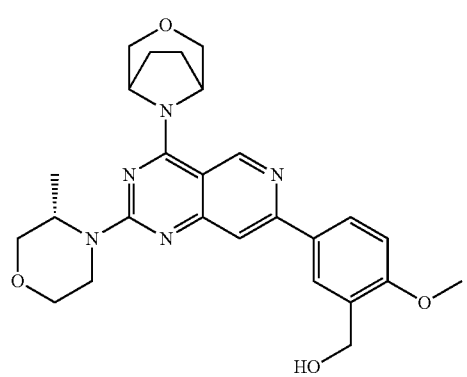
26
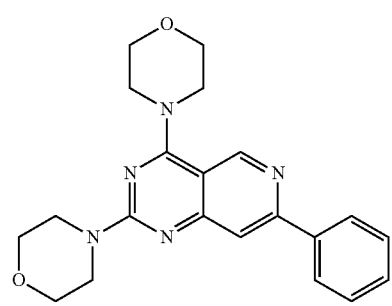
27
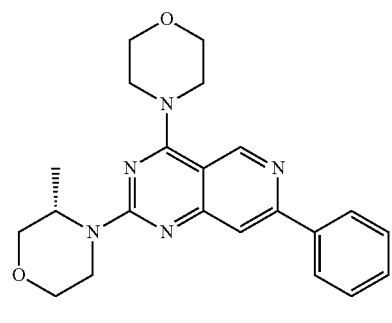

28
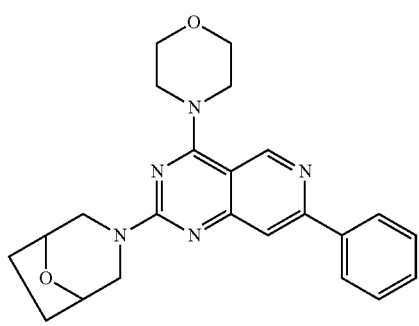
29
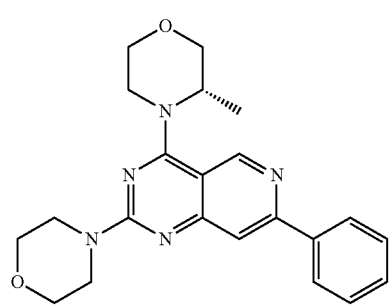
30
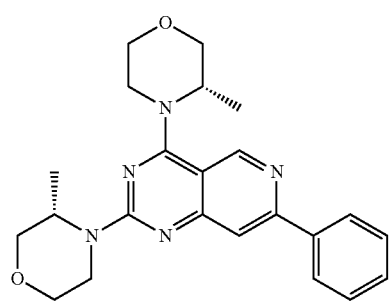
31
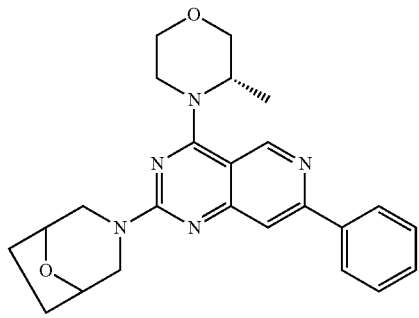
32
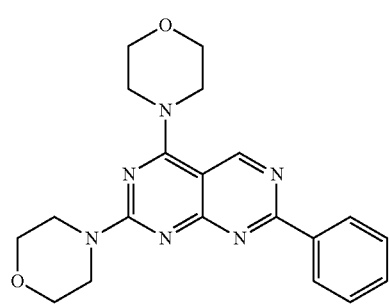
33
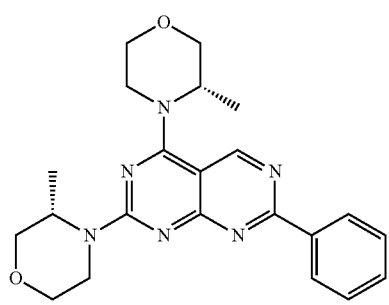
34
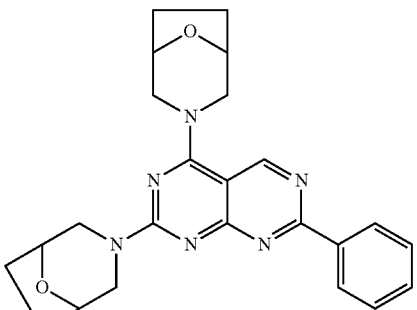
35
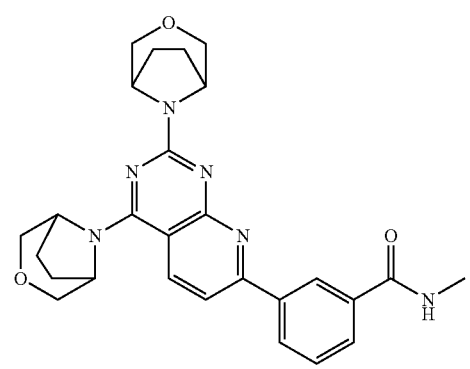
36
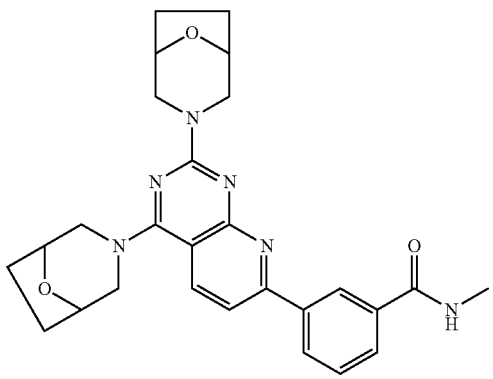

37 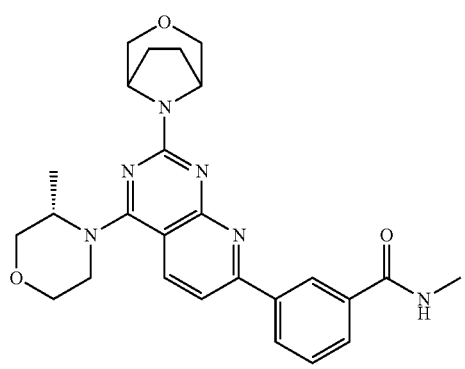
38 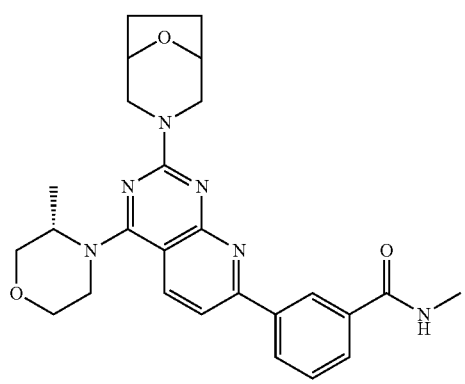
39 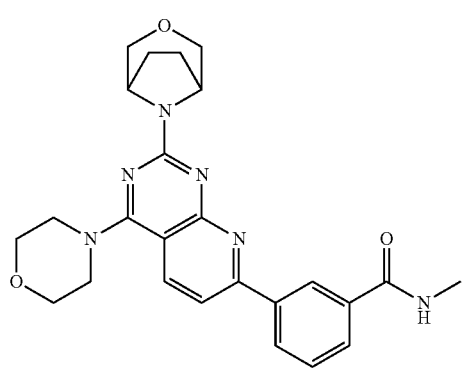
40 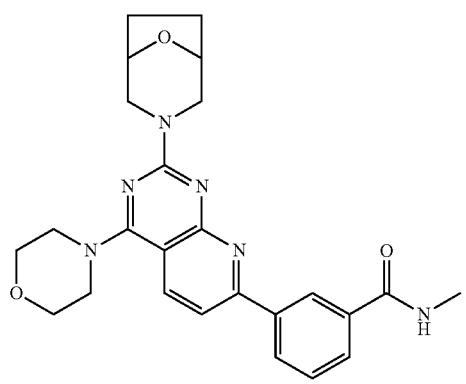
41 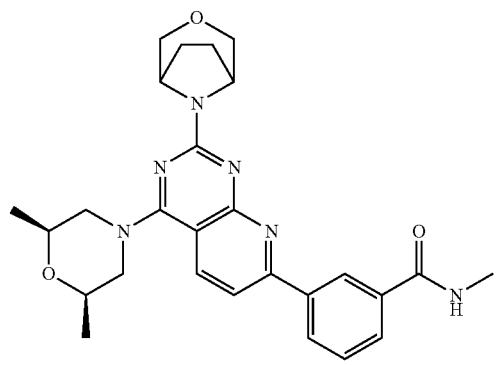
42 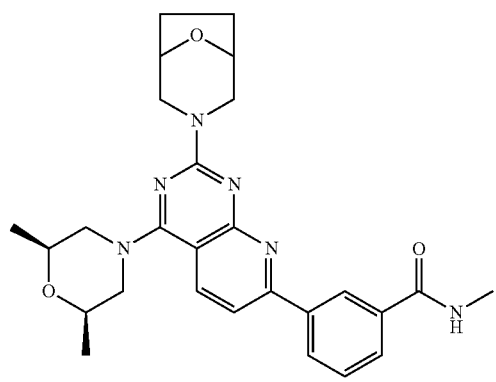
43 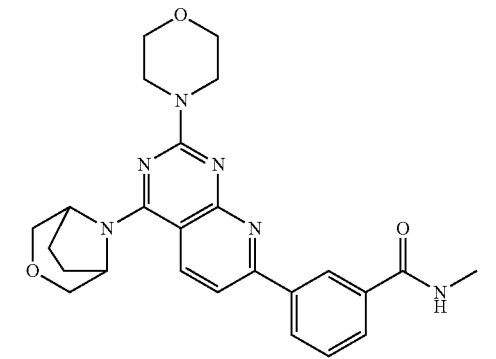
44 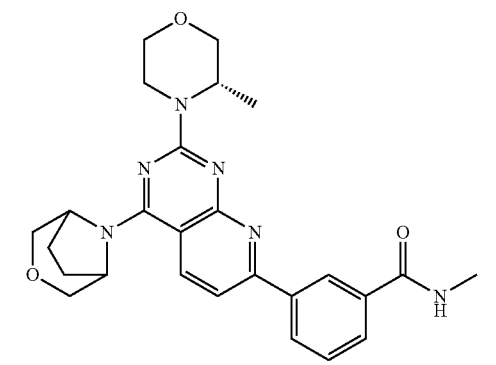

45
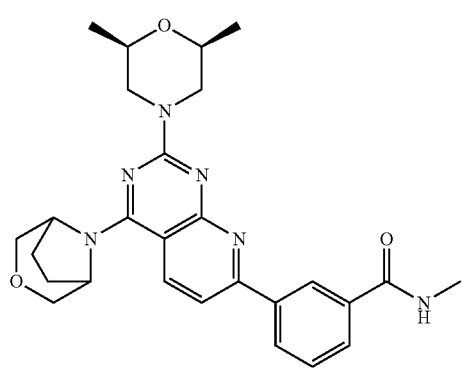
46
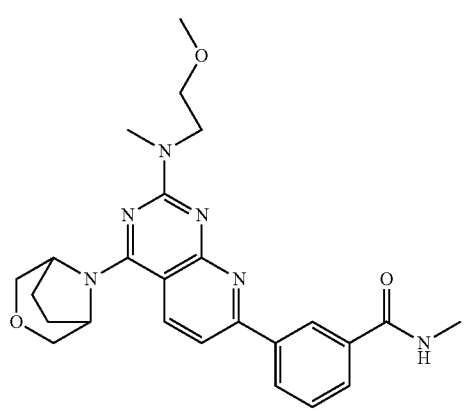
47
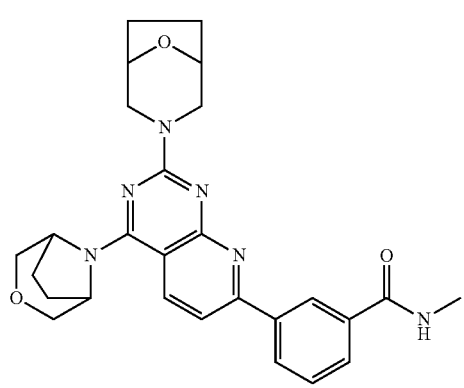
48
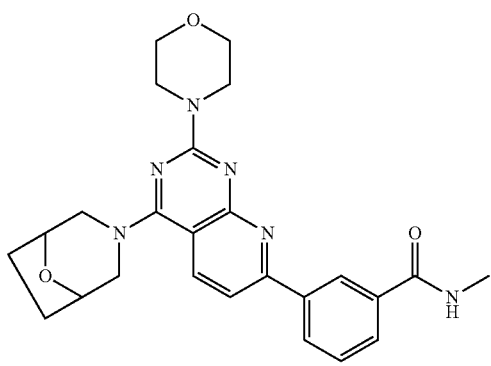
49
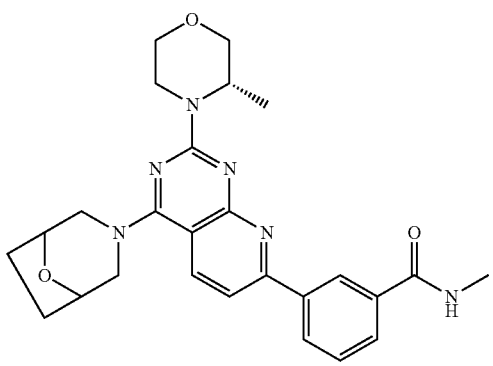
50
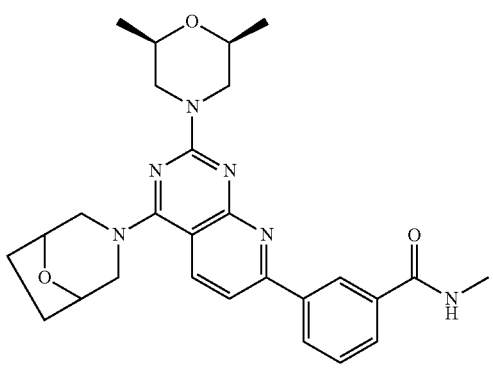
51
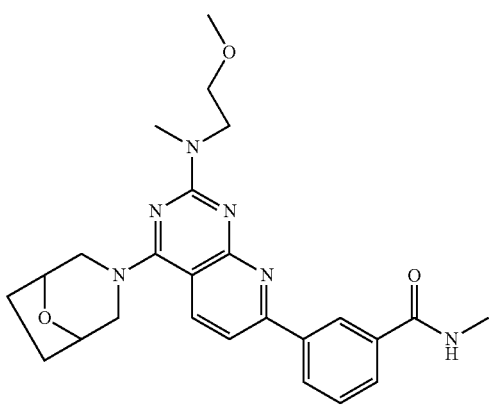
52
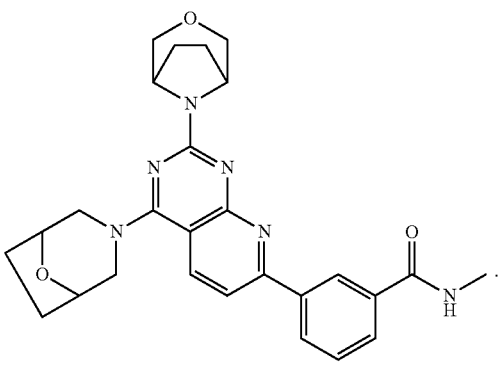
The pharmaceutically acceptable salt of the pyridopyrimidine or pyrimidopyrimidine compounds represented by formula (I) in present invention may be prepared by dissolving the pyridopyrimidine or pyrimidopyrimidine compound represented by formula (I) in an alcohol solution saturated with an acid corresponding to the salt to perform reaction, for example, the pyridopyrimidine or pyrimidopyrimidine compound provided by present invention may be dissolved in a methanol solution saturated with HCl, agitating at room temperature for 30 mins, and then evaporating off solvent to dryness to obtain the corresponding hydrochloride.

Unless otherwise indicated, among the following reaction schemes, all the symbols in the compounds have the same meaning as that in formula (I). The compounds in the reaction schemes may include the salts thereof, for example, the salts defined by the compounds having the structure of formula (I), and the like.

For illustrative purpose, the reaction schemes shown below provide possible ways for synthesizing the compounds of the present invention as well as key intermediates. More detailed description of the individual reaction steps can be found in the following Examples. Those skilled in the art will understand that other synthetic routes may be used in the synthesis of the compounds of the present invention. Although the reaction schemes shown and described hereafter involve specific starting materials and reagents, they could be readily replaced with other starting materials and reagents to provide a variety of derivatives and/or reaction conditions. In addition, in view of the disclosure of the present invention, the compounds prepared by the method can be further modified using conventional chemical methods well known to a person skilled in the art.

The substituted pyrido[2,3-d]pyrimidine compound represented by formula (Ia), or the isomer, the pharmaceutically acceptable salt, the ester, the prodrug or the solvate thereof can be prepared by the following method, and regarding the specific reagents and reaction conditions in the reaction, reference can be made to Example 1.

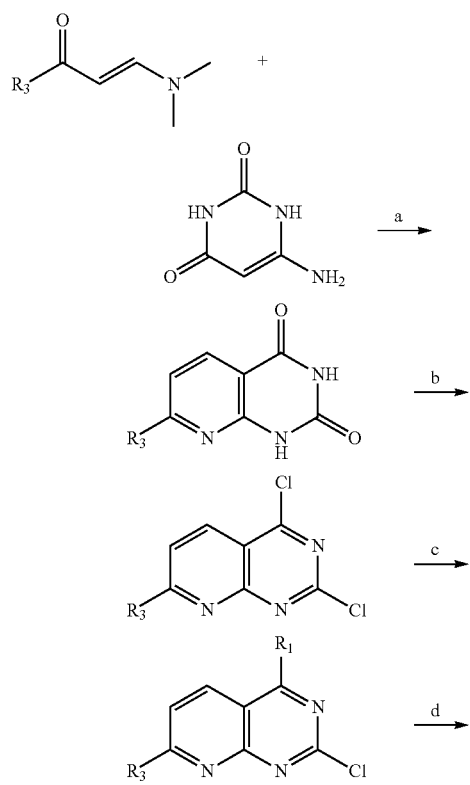

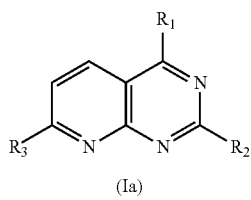

(Ia)

The substituted pyrido[4,3-d]pyrimidine compound represented by formula (Ib), the isomer, the pharmaceutically acceptable salt, the ester, the prodrug or the solvate thereof can be prepared by the following method, and regarding the specific reagents and reaction conditions in the reaction, reference can be made to Example 13.

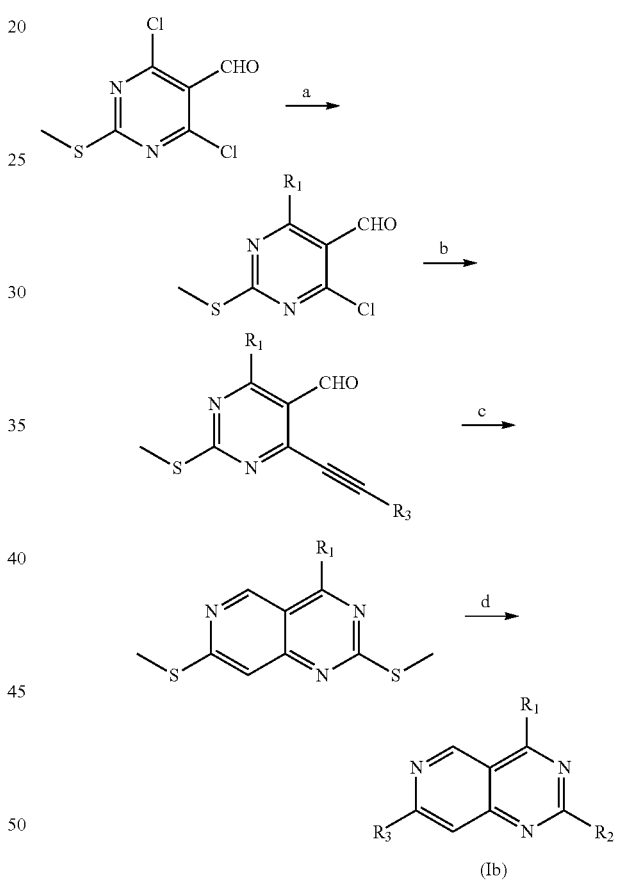

(Ib)

The substituted pyrimido[4,5-d]pyrimidine compound represented by formula (Ic), the isomer thereof, the pharmaceutically acceptable salt, the ester, the prodrug or the solvate thereof can be prepared by the following method, and regarding the specific reagents and reaction conditions in the reaction, reference can be made to Example 32.

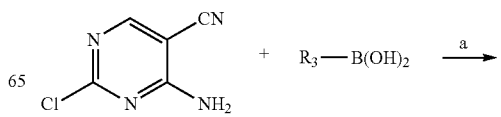

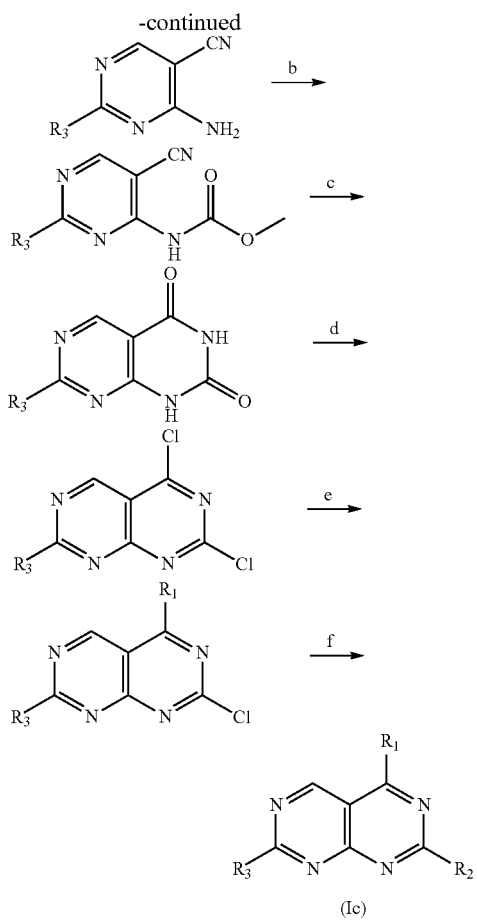

According to another aspect of present invention, provided is a use of the pyridopyrimidine or pyrimidopyrimidine compound represented by formula (I), the isomer, the pharmaceutically acceptable salt, the ester, the prodrugs or the solvate thereof as a mTOR inhibitor, and a use in treating a disease or condition caused by dysfunction of PI3K-AKT-mTOR signaling pathway, especially a tumor disease. Specifically, the tumor disease includes, but not limited to melanoma, liver cancer, kidney cancer, acute leukemia, non-small cell lung cancer, prostate cancer, thyroid cancer, skin cancer, colon cancer, rectal cancer, pancreatic cancer, ovarian cancer, breast cancer, myelodysplastic syndrome, esophageal cancer, gastrointestinal cancer and mesothelioma.

According to another aspect of the present invention, also provided is a pharmaceutical composition comprising one or more selected from the group consisting of the pyridopyrimidine or pyrimidopyrimidine compound represented by formula (I), the isomer, the pharmaceutically acceptable salt, the ester, the prodrug or the solvate thereof, which can be used as a mTOR inhibitor, and the pharmaceutical composition may optionally comprise a pharmaceutically acceptable carrier or excipient.

The pharmaceutically acceptable carrier refers to a conventional pharmaceutical carrier in the pharmaceutical art, for example, a diluent, such as water and the like; a filler, such as starch, sucrose and the like; a binder such as a cellulose derivative, an alginate, gelatin, polyvinylpyrrolidone; a wetting agent, such as glycerol; a disintegrating agent, such as agar, calcium carbonate, and sodium bicarbonate; an absorbefacient, such as a quaternary ammonium compound; a surfactant, such as cetyl alcohol; an adsorption carrier, such as kaolin and bentonite; a lubricant, such as talc, calcium stearate and magnesium stearate, and polyethylene glycol and the like. In addition, other adjuvants such as a flavoring agent and a sweetening agent, etc., can also be added into the pharmaceutical composition.

According to another aspect of present invention, also provided is a method for treating disease or condition caused by dysfunction of PI3K-AKT-mTOR signaling pathway, especially a tumor disease, wherein the method comprises administering a therapeutically effective amount of one or more selected from a group consisting of the pyridopyrimidine or pyrimidopyrimidine compound represented by formula (I), the isomer, the pharmaceutically acceptable salt, the ester, the prodrug or the solvate thereof, or the above pharmaceutical composition of present invention to a patient.

The compound or the pharmaceutical composition provided in present invention may be administered orally, rectally or parenterally to a patient in need of such treatment. When administered orally, they can be made into a conventional solid preparation such as tablet, powder, granule, capsule, etc., or into a liquid preparation, such as a water or oil suspension, or other liquid preparation such as syrup and the like; and when administrated parenterally, they may be made into an injectable solution, an aqueous or oily suspension and the like.

Advantageous Effect

The compounds of present invention show good inhibitory activity on mTOR, and also show strong proliferation inhibition effect on human glioma U87MG and human prostate cancer LNCap cells, wherein the compounds having the best activities, such as compound 1, compound 3 and compound 8, have comparative activities as that of the similar compound in clinical trials in the prior art, such as AZD8055.

DETAILED DESCRIPTION OF EXEMPLARY EMBODIMENT

It can be understood that a person skilled in the art could make best use of present invention with the aid of foregoing description without further details. Thus, the following examples are provided merely to further illustrate the present invention and do not intend to limit the scope of the present invention in any way.

The starting materials are commercially available products, or can be prepared by a method known in the art, or prepared according to a method described herein.

Structures of the compounds were identified by nuclear magnetic resonance ($^1$H-NMR) spectra and/or mass spectrometry (MS). NMR measurement was conducted on a Varian AMX-400 type NMR apparatus, the solvent used for the measurement was deuterated chloroform ($CDCl_3$) or deuterated dimethylsulfoxide (DMSO-D6), and TMS was used as the internal standard. MS measurement was conducted on a Thermo Finnigan LCQ-Deca XP type (ESI) Liquid chromatograph-Mass spectrometer. An ISCO CombiFlash® Rf 75 flash chromatography instrument was used for the column chromatography purification of the products, and the supporter was 200-300 mesh silica gel from Qingdao Haiyang Chemical Co Ltd. Biotage Initiator microwave synthesizer was used to perform microwave heating.

EXAMPLES

Example 1: Preparation of 5-(2,4-di(3-oxa-8-azabicyclo[3.2.1]octan-8-yl)pyrido[2,3-d]pyrimidin-7-yl)-2-methoxyphenylmethanol (Compound 1)

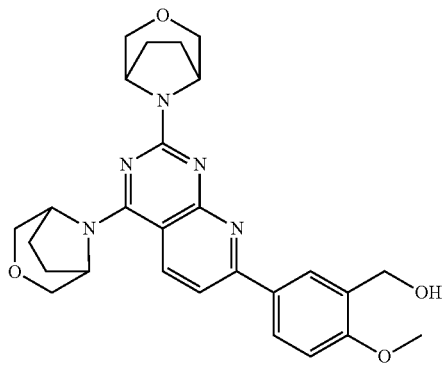

The reaction scheme was as follows:

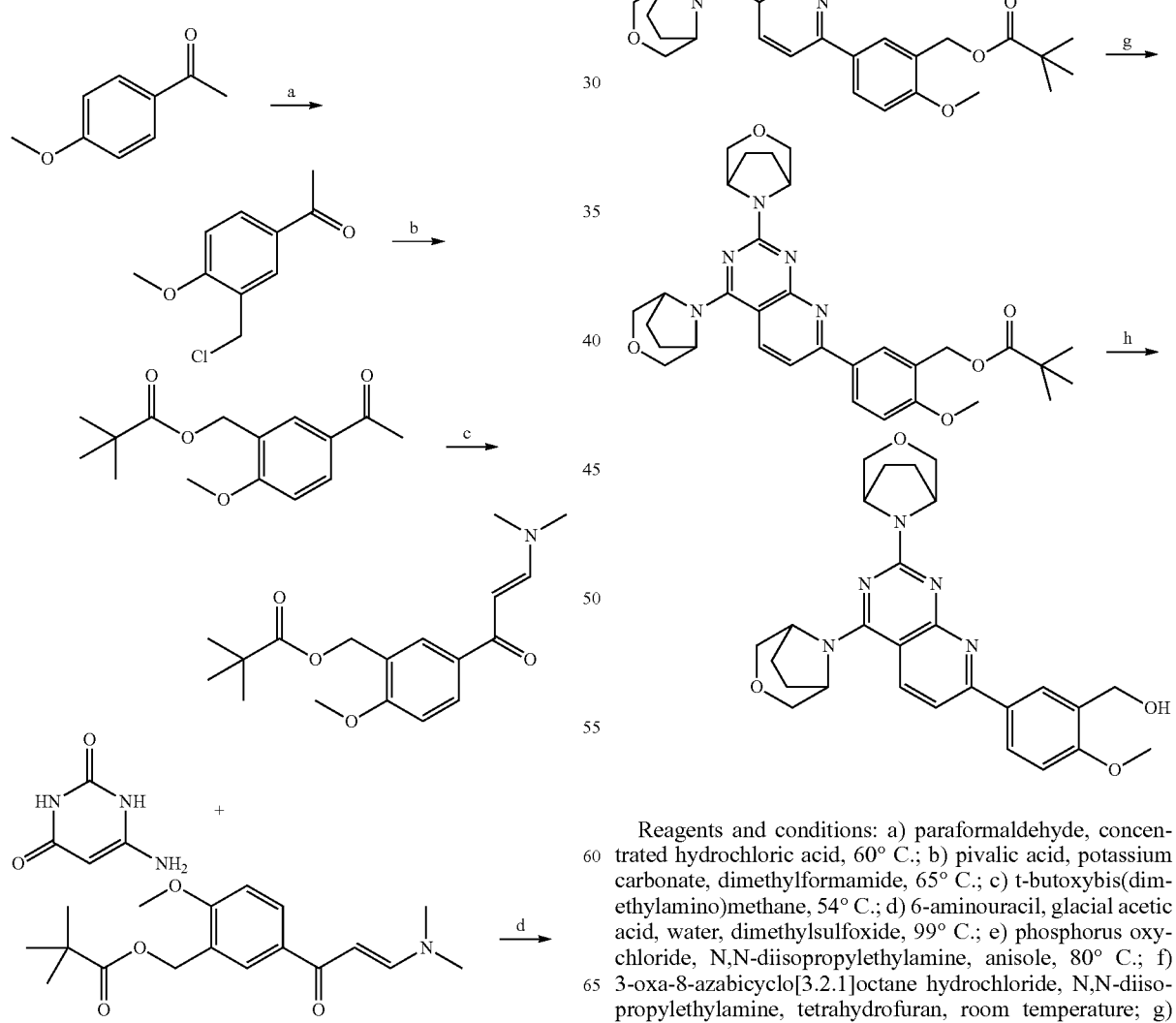

Reagents and conditions: a) paraformaldehyde, concentrated hydrochloric acid, 60° C.; b) pivalic acid, potassium carbonate, dimethylformamide, 65° C.; c) t-butoxybis(dimethylamino)methane, 54° C.; d) 6-aminouracil, glacial acetic acid, water, dimethylsulfoxide, 99° C.; e) phosphorus oxychloride, N,N-diisopropylethylamine, anisole, 80° C.; f) 3-oxa-8-azabicyclo[3.2.1]octane hydrochloride, N,N-diisopropylethylamine, tetrahydrofuran, room temperature; g) 3-oxa-8-azabicyclo[3.2.1]octane hydrochloride, N,N-diisopropylethylamine, isopropanol, microwave, 160° C., 80 mins; h) potassium hydroxide, tetrahydrofuran, methanol, room temperature.

a) 1-(3-(chloromethyl)-4-methoxyphenyl)ethanone

To p-methoxyacetophenone (1.0 g, 6.65 mmol), paraformaldehyde (362 mg, 11.97 mmol) and concentrated hydrochloric acid (10.5 mL) were added, and stirred overnight under 60° C. The reaction mixture was then cooled to room temperature, poured onto crushed ice, extracted with ethyl acetate, washed successively with water, saturated sodium bicarbonate aqueous solution, brine, dried over anhydrous sodium sulfate, and distilled off the organic solvent under reduced pressure to give 1.2 g of the title compound as a gray solid with a yield of 92%.
$^1$H NMR (400 MHz, CDCl$_3$): δ 8.03-7.91 (m, 2H), 6.94 (dd, J=8.6, 2.0 Hz, 1H), 4.67 (s, 2H), 3.95 (s, 3H), 2.57 (s, 3H).

b) 5-acetyl-2-methoxybenzyl pivalate

Pivalic acid (868.4 mg, 8.51 mmol), potassium carbonate (1.2 g, 8.70 mmol) was dissolved in dimethylformamide, and 1-(3-(chloromethyl)-4-methoxyphenyl)ethanone (1.2 g, 6.06 mmol) obtained as above dissolved in 3 mL of dimethylformamide was added thereto under argon. The mixture was heated to 65° C. and reacted for 4 hours, added with water, extracted with ethyl acetate, washed with water, dried over anhydrous sodium sulfate, and concentrated under reduced pressure. The residue was purified by flash silica gel column chromatography eluting with petroleum ether/ethyl acetate (V/V=8:1) to afford 1.4 g of the title compound as a yellow oil with a yield of 87.5%.
MS(EI): 264.
$^1$H NMR (400 MHz, CDCl$_3$) δ 8.01-7.88 (m, 2H), 6.92 (d, J=9.1 Hz, 1H), 5.17 (s, 2H), 3.91 (s, 3H), 2.56 (s, 3H), 1.27 (s, 9H).

c) (E)-5-(3-(dimethylamino)acryl)-2-methoxybenzyl pivalate

To 5-acetyl-2-methoxybenzyl pivalate (750 mg, 30 mmol) obtained as above, tert-butoxy-bis(dimethylamino)methane (2 g, 12 mmol) was added. The mixture was reacted at 54° C. for 6 hours, added with water, extracted with ethyl acetate, washed with water, dried over anhydrous sodium sulfate, and concentrated under reduced pressure to afford 900 mg of the title compound as a yellow oil with a yield of 94%.
MS(ESI): 320(M+1), the compound was used in the next step without further purification.

d) 5-(2,4-dioxo-1,2,3,4-tetrahydropyrido[2,3-d]pyrimidin-7-yl)-2-methoxybenzyl pivalate 6-aminouracil (726 mg, 5.71 mmol) was added to glacial acetic acid (7.1 mL) and water (1.8 mL), and heated to 99° C. (E)-5-(3-(dimethylamino)acryl)-2-methoxybenzyl pivalate obtained as above was dissolved in 2.7 mL of dimethylsulfoxide, and the resultant solution was added dropwise within 80 mins to the above mixture and reacted at 99° C. for 3 hours. The reaction mixture was cooled to 0° C., and 7 g of potassium hydroxide dissolved in 14 mL of water was added thereto under an ice bath (pH=7), followed by addition of an aqueous potassium carbonate solution to adjust the mixture to pH=9 to 10. The mixture was stirred at room temperature overnight. Beige precipitate was precipitated and filtered, and the solid was washed with an aqueous potassium carbonate solution. Then the resultant solid was dissolved in a citric acid solution under agitating for 2 hours (pH=4), filtered, washed with water until to be neutral to give 864 mg of the title compound as a yellow solid with a yield of 40%.
ESI: 384(M+1). $^1$H NMR (400 MHz, DMSO) δ 11.67 (s, 1H), 11.42 (s, 1H), 8.27 (d, J=8.2 Hz, 1H), 8.17 (dd, J=8.7, 2.3 Hz, 1H), 8.11 (d, J=2.3 Hz, 1H), 7.75 (d, J=8.3 Hz, 1H), 7.22 (d, J=8.8 Hz, 1H), 5.13 (s, 2H), 3.89 (s, 3H), 1.18 (s, 9H).

d) 5-(2,4-dichloropyrido[2,3-d]pyrimidin-7-yl)-2-methoxybenzyl pivalate 5-(2,4-dioxo-1,2,3,4-tetrahydropyrido[2,3-d]pyrimidin-7-yl)-2-methoxybenzyl pivalate (800 mg, 2.09 mmol) obtained as above was dissolved in anisole, and added with N,N-diisopropylethylamine (675 mg, 5.22 mmol), and then with phosphorus oxychloride (963 mg, 6.26 mmol). After agitated at room temperature for 1.5 hours, the reaction mixture was heated to 80° C., and then reacted for 4.5 hours at 80° C. Afterwards, phosphorus oxychloride and part of solvent was removed under reduced pressure, and 4 mL of 2M dipotassium hydrogen carbonate and ethyl acetate were added. The mixture was rested overnight and filtered, and the solid was washed with ethyl acetate to give 700 mg of the title compound as a yellow solid.
MS(ESI): 420(M+1), the compound was used in the next step without further purification.

f) 5-(4-(3-oxa-8-azabicyclo[3.2.1]octan-8-yl)-2-chloropyrido[2,3-d]pyrimidin-7-yl)-2-methoxybenzyl pivalate 3-oxa-8-azabicyclo[3.2.1]octane hydrochloride (490 mg, 3.27 mmol) was dissolved in 30 mL of tetrahydrofuran, added with N,N-diisopropylethylamine (425 mg, 3.29 mmol), and reacted at room temperature for 2 hours. The resultant mixture was then added to 5-(2,4-dichloropyrido[2,3-d]pyrimidin-7-yl)-2-methoxybenzyl pivalate obtained as above (580 mg, 1.62 mmol), which was dissolved in 30 mL of tetrahydrofuran, added with N,N-diisopropylethylamine (425 mg, 3.29 mmol), and reacted at room temperature overnight. The mixture was removed off solvent under reduced pressure, added with water, extracted with ethyl acetate, dried over anhydrous sodium sulfate, and concentrated under reduced pressure. The residue was purified by flash silica gel column chromatography eluting with petroleum ether/ethyl acetate (V/V=1:1) to give 560 mg of the title compound as a yellow solid with a yield of 82.0%.
MS(ESI): 497(M+1).
$^1$H NMR (400 MHz, CDCl$_3$) δ 8.36 (dd, J=8.7, 2.4 Hz, 1H), 8.19 (dd, J=17.3, 5.5 Hz, 2H), 7.78 (d, J=8.7 Hz, 1H), 7.01 (s, 1H), 5.21 (s, 2H), 4.84 (s, 2H), 4.00 (d, J=10.9 Hz, 2H), 3.92 (s, 3H), 3.81 (d, J=10.9 Hz, 2H), 2.21-2.09 (m, 2H), 2.09-1.98 (m, 2H), 1.30-1.15 (m, 9H).

g) 5-(2,4-di(3-oxa-8-azabicyclo[3.2.1]octan-8-yl)pyrido[2,3-d]pyrimidin-7-yl)-2-methoxybenzyl pivalate 5-(4-(3-oxa-8-azabicyclo[3.2.1]octan-8-yl)-2-chloropyrido[2,3-d]pyrimidin-7-yl)-2-methoxybenzyl pivalate (78 mg, 0.157 mmol) obtained as above was dissolved in 2 mL of isopropanol, added with N,N-diisopropylethylamine (42.9 mg, 0.32 mmol), and then with 3-oxa-8-azabicyclo[3.2.1]octane hydrochloride (36 mg, 0.238 mmol). The mixture was reacted in microwave at 160° C. for 80 mins, evaporated off the solvent to give about 70 mg of an earthy yellow solid. The product was used in the next step without further purification.

h) 5-(2,4-di(3-oxa-8-azabicyclo[3.2.1]octan-8-yl)pyrido[2,3-d]pyrimidin-7-yl)-2-methoxyphenyl methanol To 70 mg of 5-(2,4-di(3-oxa-8-azabicyclo[3.2.1]octan-8-yl)-pyrido[2,3-d]pyrimidin-7-yl)-2-methoxybenzyl pivalate obtained as above, 5 mL of methanol, 3 mL of tetrahydrofuran and about 80 mg of potassium hydroxide were added, and reacted at room temperature overnight. The mixture was removed off the solvent under reduced pressure, added with water, extracted with ethyl acetate, dried over anhydrous sodium sulfate, and concentrated under reduced pressure. The residue was purified by flash silica gel column chromatography eluting with petroleum ether/ethyl acetate (V/V=1:2) to give 30 mg of the title compound as a yellow solid with a yield of 50.0%.

MS(ESI): m/z 490[M+H]$^+$.

$^1$H NMR (400 MHz, CDCl$_3$) δ 8.21-8.13 (m, 2H), 8.06 (d, J=8.3 Hz, 1H), 7.46 (d, J=8.3 Hz, 1H), 6.99 (d, J=8.4 Hz, 1H), 4.78 (s, 2H), 4.58 (s, 2H), 4.17 (s, 1H), 4.04-3.97 (m, 3H), 3.94 (s, 3H), 3.77-3.68 (m, 5H), 3.49 (s, 1H), 2.17-1.93 (m, 8H).

Example 2: Preparation of 5-(2,4-di(8-oxa-3-azabicyclo[3.2.1]octan-3-yl)pyrido[2,3-d]pyrimidin-7-yl)-2-methoxyphenyl methanol (Compound 2)

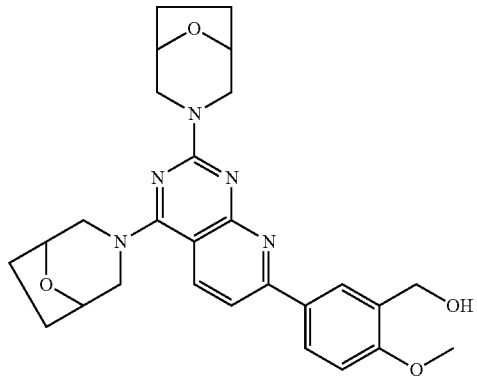

2

The title compound was prepared in the same manner as that in Example 1, and steps a, b, c, d, e and h were the same as those in Example 1, except that 3-oxa-8-azabicyclo[3.2.1]octane hydrochloride in steps f and g was replaced with 8-oxa-3-azabicyclo[3.2.1]octane hydrochloride. The title compound was obtained as a yellow solid with a yield of 38.0%.

MS(ESI): m/z 490[M+H]$^+$.

Example 3: Preparation of 5-(4-(3-oxa-8-azabicyclo[3.2.1]octan-8-yl)-2-((S)-3-methylmorpholine)pyrido[2,3-d]pyrimidin-7-yl)-2-methoxyphenylmethanol (Compound 3)

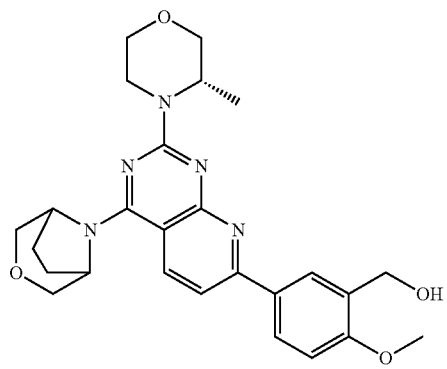

3

The title compound was prepared as the same manner in that in Example 1, and steps a, b, c, d, e, f and h were the same as those in Example 1, except that 3-oxa-8-azabicyclo[3.2.1]octane hydrochloride in step g was replaced with (S)-3-methylmorpholine. The title compound was obtained as a yellow solid with a yield of 64%.

MS(ESI): m/z 478[M+H]$^+$.

Example 4: Preparation of 5-(4-(3-oxa-8-azabicyclo[3.2.1]octan-8-yl)-2-morpholinylpyrido[2,3-d]pyrimidin-7-yl)-2-methoxyphenylmethanol (Compound 4)

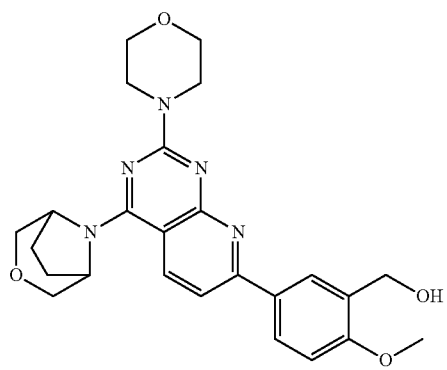

4

The title compound was prepared in the same manner as that in Example 1, and steps a, b, c, d, e, f and h were the same as those in Example 1, except that 3-oxa-8-azabicyclo[3.2.1]octane hydrochloride in step g was replaced with morpholine. The title compound was obtained as a yellow solid with a yield of 47%.

MS(ESI): m/z 464[M+H]$^+$.

Example 5: Preparation of 5-(4-(3-oxa-8-azabicyclo[3.2.1]octan-8-yl)-2-((2S,6R)-2,6-dimethylmorpholine)pyrido[2,3-d]pyrimidin-7-yl)-2-methoxyphenylmethanol (Compound 5)

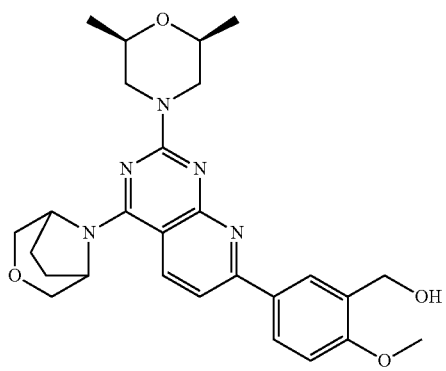

The title compound was prepared in the same manner as that in Example 1, and steps a, b, c, d, e, f and h were the same as those in Example 1, except that 3-oxa-8-azabicyclo[3.2.1]octane hydrochloride in step g was replaced with (2S,6R)-2,6-dimethylmorpholine. The title compound was obtained as a yellow solid with a yield of 79%.

MS(ESI): m/z 492[M+H]$^+$.

Example 6: Preparation of 5-(4-(3-oxa-8-azabicyclo[3.2.1]octan-8-yl)-2-((2-methoxyethyl)methylamino)pyrido[2,3-d]pyrimidin-7-yl)-2-methoxyphenylmethanol (Compound 6)

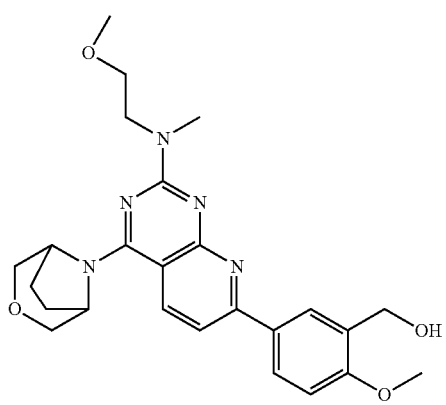

The title compound was prepared in the same manner as that in Example 1, and steps a, b, c, d, e, f and h were the same as those in Example 1, except that 3-oxa-8-azabicyclo[3.2.1]octane hydrochloride in step g was replaced with 2-methoxy-N-methylethylamine. The title compound was obtained as a yellow solid with a yield of 80%.

MS(ESI): m/z 466[M+H]$^+$.

Example 7: Preparation of 5-(2-(8-oxa-3-azabicyclo[3.2.1]octan-3-yl)-4-((3-oxa-8-azabicyclo[3.2.1]octan-8-yl)pyrido[2,3-d]pyrimidin-7-yl)-2-methoxyphenylmethanol (Compound 7)

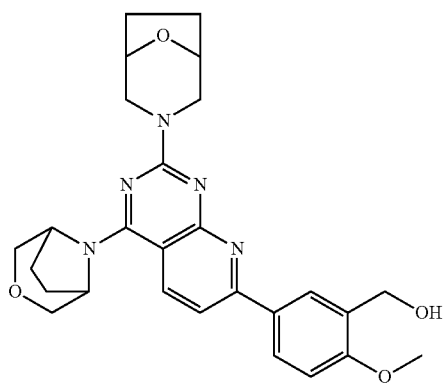

The title compound was prepared in the same manner as that in Example 1, and steps a, b, c, d, e, f and h were the same as those in Example 1, except that 3-oxa-8-azabicyclo[3.2.1]octane hydrochloride in step g was replaced with 8-oxa-3-azabicyclo[3.2.1]octane hydrochloride. The title compound was obtained as a yellow solid with a yield of 60%.

MS(ESI): m/z 490[M+H]$^+$.

Example 8: Preparation of 5-(2-((1R,5S)-3-oxa-8-azabicyclo[3.2.1]octan-8-yl)-4-((S)-3-methylmorpholine)pyrido[2,3-d]pyrimidin-7-yl)-2-methoxyphenylmethanol (Compound 8)

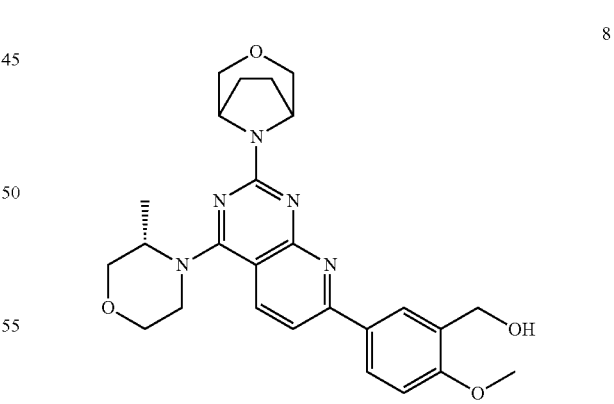

The title compound was prepared in the same manner as that in Example 1, and steps a, b, c, d, e, g and h were the same as those in Example 1, except that 3-oxa-8-azabicyclo[3.2.1]octane hydrochloride in step f was replaced with (S)-3-methylmorpholine. The title compound was obtained as a yellow solid with a yield of 82%.

MS(ESI): m/z 478[M+H]$^+$.

Example 9: Preparation of 5-(2-((1R,5S)-3-oxa-8-azabicyclo[3.2.1]octan-8-yl)-4-morpholinyl pyrido[2,3-d]pyrimidin-7-yl)-2-methoxyphenylmethanol (Compound 9)

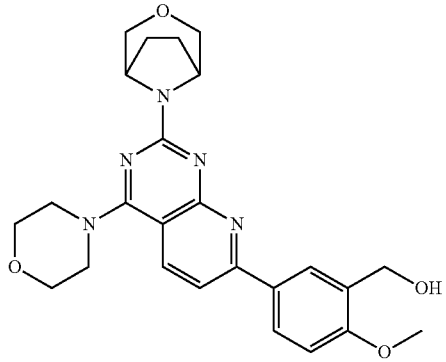

The title compound was prepared in the same manner as that in Example 1, and steps a, b, c, d, e, g and h were the same as those in Example 1, except that 3-oxa-8-azabicyclo[3.2.1]octane hydrochloride in step f was replaced with morpholine. The title compound was obtained as a yellow solid with a yield of 82%.

MS(ESI): m/z 464[M+H]$^+$.

Example 10: Preparation of 5-(2-((1R,5S)-3-oxa-8-azabicyclo[3.2.1]octan-8-yl)-4-((2S,6R)-2,6-dimethylmorpholine)pyrido[2,3-d]pyrimidin-7-yl)-2-methoxyphenylmethanol (Compound 10)

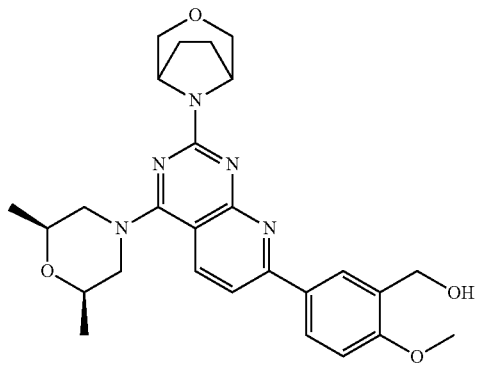

The title compound was prepared in the same manner as that in Example 1, and steps a, b, c, d, e, g and h were the same as those in Example 1, except that 3-oxa-8-azabicyclo[3.2.1]octane hydrochloride in step f was replaced with (2S,6R)-2,6-dimethylmorpholine. The title compound was obtained as a yellow solid with a yield of 48%.

MS(ESI): m/z 492[M+H]$^+$.

Example 11: Preparation of 5-(4-(8-oxa-3-azabicyclo[3.2.1]octan-3-yl)-2-((1R,5S)-3-oxa-8-azabicyclo[3.2.1]octan-8-yl)pyrido[2,3-d]pyrimidin-7-yl)-2-methoxyphenylmethanol (Compound 11)

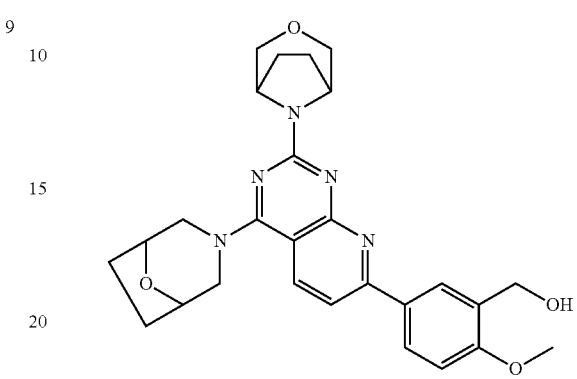

The title compound was prepared in the same manner as that in Example 1, and steps a, b, c, d, e, g and h were the same as those in Example 1, except that 3-oxa-8-azabicyclo[3.2.1]octane hydrochloride in step f was replaced with 8-oxa-3-azabicyclo[3.2.1]octane hydrochloride. The title compound was obtained as a yellow solid with a yield of 75%.

MS(ESI): m/z 490[M+H]$^+$.

Example 12: Preparation of 5-(2-((1R,5S)-3-oxa-8-azabicyclo[3.2.1]octan-8-yl)-4-((2-methoxyethyl)amino)pyrido[2,3-d]pyrimidin-7-yl)-2-methoxyphenylmethanol (Compound 12)

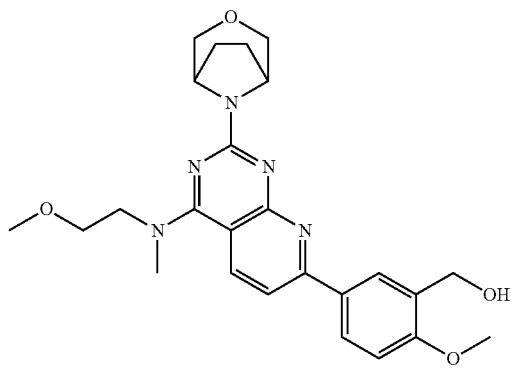

The title compound was prepared in the same manner as that in Example 1, and steps a, b, c, d, e, g and h were the same as those in Example 1, except that 3-oxa-8-azabicyclo[3.2.1]octane hydrochloride in step f was replaced with 2-methoxy-N-methyl ethyl amine, t. The title compound was obtained as a yellow solid with a yield of 75%.

MS(ESI): m/z 466[M+H]$^+$.

Example 13: Preparation of (5-(2,4-dimorpholinylpyrido[4,3-d]pyrimidin-7-yl)-2-methoxyphenyl)methanol (Compound 13)

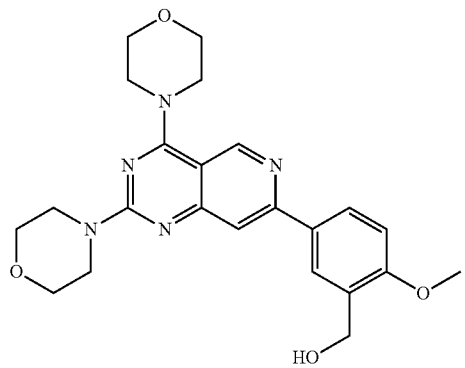

The reaction scheme was as follows:

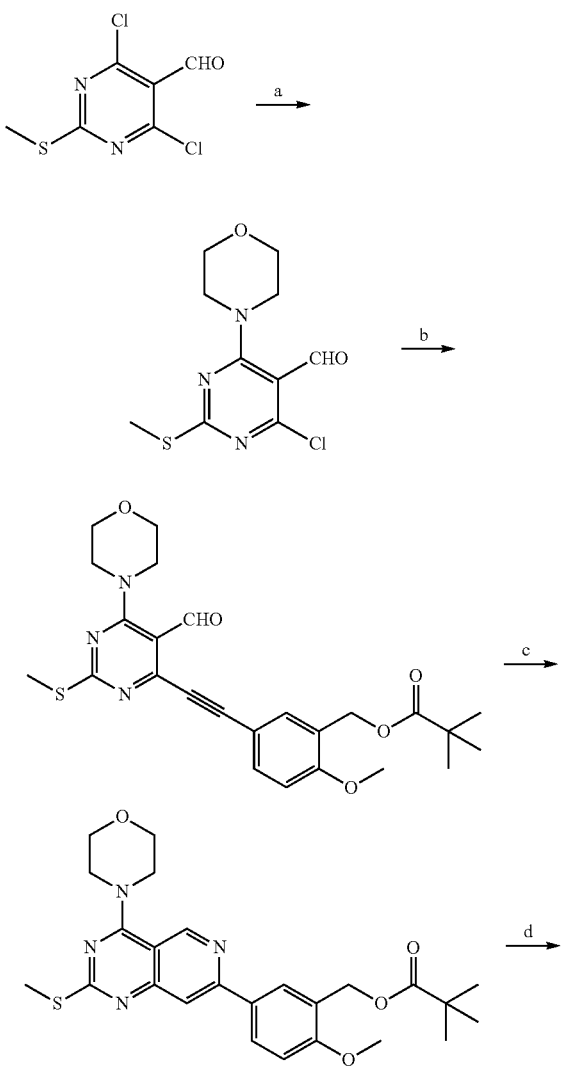

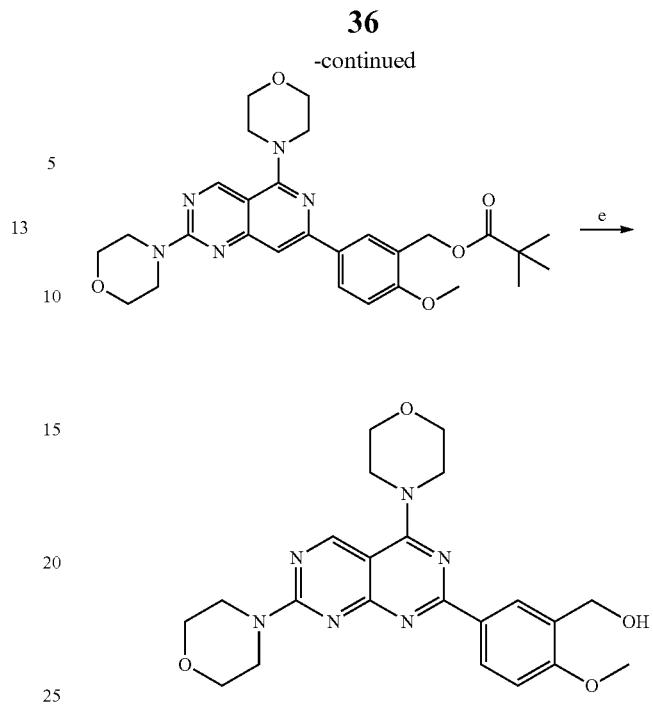

Reagents and conditions: a) morpholine, 0° C., 2 hours; b) 5-ethynyl-2-methoxybenzyl pivalate, bis(triphenylphosphine)palladium(II) dichloride, copper iodide, triethylamine, dimethylformamide, 45° C.; c) t-butylamine, 120° C.; d) i. m-chloroperbenzoic acid, dichloromethane, room temperature; ii. morpholine, dimethylsulfoxide, 75° C.; e) potassium hydroxide, tetrahydrofuran, room temperature.

a) 2-methylthio-4-chloro-6-morpholinylpyrimidine-5-carboxaldehyde 2-(methylthio)-4,6-dichloropyrimidine-5-carboxaldehyde (1.5 g, 6.76 mmol) was dissolved in 50 mL of methanol, added dropwisely with morpholine (590 g, 6.76 mmol) dissolved in 2 mL of methanol under ice bath, reacted at room temperature for 2 hours, and filtered. The solid was washed with methanol to give 1.24 g of the title compound as a yellow solid with a yield of 67%.

MS (ESI): m/z 274[M+H]+.
$^1$H NMR (400 MHz, CDCl$_3$) δ 10.21 (s, 1H), 3.88-3.76 (m, 4H), 3.72-3.54 (m, 4H), 2.52 (s, 3H).

b) 5-((5-formyl-2-(methylthio)-6-morpholinylpyrimidin-4-yl)acetenyl)-2-methoxybenzyl pivalate To 2-methylthio-4-chloro-6-morpholinylpyrimidine-5-carboxaldehyde (602 mg, 2.21 mmol) obtained as above, 5 mL of dimethylformamide, 5-acetenyl-2-methoxybenzyl pivalate (814 mg, 3.31 mmol), copper iodide (13 mg, 0.066 mmol) and triethylamine (668 mg, 6.61 mmol) were added. The mixture was bubbled with Argon for several minutes, added with bis(triphenylphosphine)palladium(II) dichloride, reacted at 45° C. overnight, added with water, and extracted with ethyl acetate three times. The combined organic phase was dried over anhydrous sodium sulfate, and concentrated under reduced pressure. The residue was purified by flash silica gel column chromatography eluting with petroleum ether/ethyl acetate (V/V=2:1) to give 604 mg of the title compound as a yellow solid with a yield of 57.0%.

$^1$H NMR (400 MHz, CDCl$_3$) δ 10.43 (s, 1H), 7.57 (s, 1H), 6.90 (s, 1H), 6.88 (s, 1H), 5.12 (s, 2H), 3.88 (s, 3H), 3.83-3.69 (m, 8H), 2.54 (s, 3H), 1.26 (s, 9H).

c) 2-methoxy-5-(2-(methylthio)-4-morpholinylpyrido[4,3-d]pyrimidin-7-ylbenzyl pivalate To 5-((5-formyl-2-(methylthio)-6-morpholinylpyrimidin-4-yl)acetenyl)-2-methoxy benzyl pivalate (590 mg, 1.22 mmol) obtained as above, 40 mL of tert-butylamine was added, and a sealed tube reaction was preformed overnight at 120° C. The reaction mixture was concentrated under reduced pressure, and the residue was purified by flash silica gel column chromatography eluting with petroleum ether/ethyl acetate (V/V=2:1) to give 389 mg of the title compound as a yellow solid with a yield of 66.0%.

MS (ESI): m/z, 483[M+H]$^+$.

$^1$H NMR (400 MHz, CDCl$_3$) δ 8.18-8.04 (m, 3H), 7.82 (d, J=0.7 Hz, 1H), 7.01 (d, J=8.6 Hz, 1H), 5.21 (s, 2H), 4.00-3.94 (m, 4H), 3.91 (s, 3H), 3.91-3.88 (m, 4H), 2.62 (s, 3H), 1.25 (s, 9H).

d) 5-(2,4-dimorpholinylpyrido[4,3-d]pyrimidin-7-yl)-2-methoxybenzyl pivalate

To 2-methoxy-5-(2-(methylthio)-4-morpholinylpyrido[4,3-d]pyrimidin-7-ylbenzyl pivalate (258 mg, 0.54 mmol) obtained as above, 3 mL of dichloromethane and metachloroperbenzoic acid (369 mg, 2.14 mmol) were added. The mixture was reacted at room temperature for 5 hours, concentrated under reduced pressure to remove the solvent, added with an appropriate amount of saturated aqueous solution of sodium bicarbonate, extracted with ethyl acetate, dried over anhydrous sodium sulfate, and concentrated under reduced pressure. The residue without further purification was added with 10 mL of dimethylsulfoxide to be dissolved, then with 250 mg of morpholine, reacted at 75° C. overnight, added with water, extracted with ethyl acetate, dried over anhydrous sodium sulfate, and concentrated under reduced pressure to give 85 mg of the title compound as a yellow solid with a total yield in two steps of 57.0%.

MS (ESI): m/z, 522[M+1-1]$^+$, the compound was used in subsequent step without further purification.

e) (5-(2,4-dimorpholinylpyrido[4,3-d]pyrimidin-7-yl)-2-methoxyphenyl) methanol

The 5-(2,4-dimorpholinylpyrido[4,3-d]pyrimidin-7-yl)-2-methoxybenzyl pivalate (28 mg, 0.048 mmol) obtained as above was dissolved in 3 mL of tetrahydrofuran, added with about 30 mg of potassium hydroxide, reacted for 7 hours at room temperature, removed the solvent under reduced pressure, and added with water. The resultant mixture was extracted with ethyl acetate, dried over anhydrous sodium sulfate, and concentrated under reduced pressure. The residue was separated with silica gel plate, and the product was collected and eluted with petroleum ether/ethyl acetate (V/V=1:3) to give 5 mg of the title compound as a yellow solid with a yield of 47.0%.

MS (ESI): m/z, 438[M+1-1]$^+$.

Example 14: Preparation of (S)-(2-methoxy-5-(2-(3-methylmorpholinyl-4-morpholinyl)pyrido[4,3-d]pyrimidin-7-yl)phenyl)methanol (Compound 14)

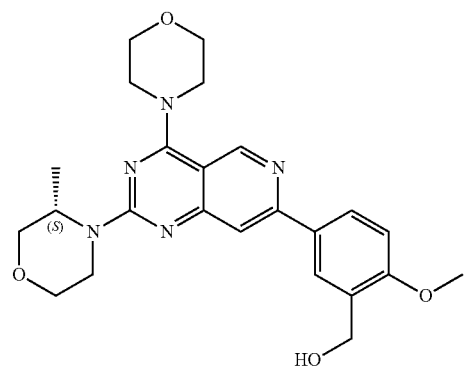

The title compound was prepared in the same manner as that in Example 13, and steps a, b, c, and e were the same as those in Example 13, except that morpholine in step d was replaced with (S)-3-methylmorpholine. The title compound was obtained as a yellow solid with a yield of 50%.

MS (ESI): m/z, 452[M+H]$^+$.

Example 15: Preparation of 5-(2-((2S,6R)-2,6-dimethylmorpholinyl-4-morpholinyl)pyrido[4,3-d]pyrimidin-7-yl)-2-methoxyphenyl)methanol (Compound 15)

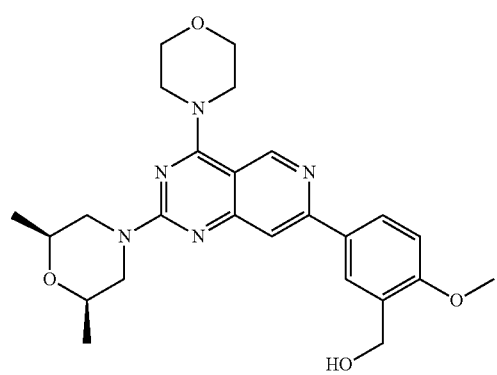

The title compound was prepared in the same manner as that in Example 13, and steps a, b, c, and e were the same as those in Example 13, except that morpholine in step d was replaced with (2S,6R)-2,6-dimethyl morpholine. The title compound was obtained as a yellow solid with a yield of 52%.

MS (ESI): m/z, 466[M+H]$^+$.

Example 16: Preparation of 5-(4-((2S,6R)-2,6-dimethyl morpholinyl-2-((S)-3-methylmorpholinyl)pyrido[4,3-d]pyrimidin-7-yl)-2-methoxyphenyl)methanol (Compound 16)

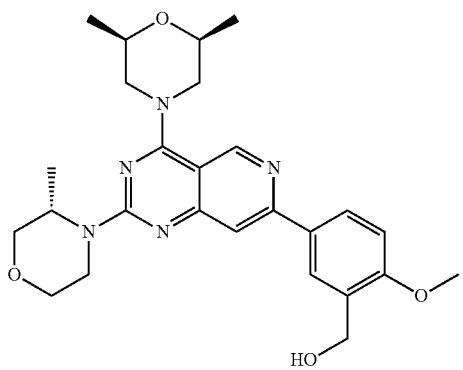

The title compound was prepared in the same manner as that in Example 13, and steps b, c, and e were the same as those in Example 13, except that morpholine in step a was replaced with (2S,6R)-2,6-dimethyl morpholine and morpholine in step d was replaced with (S)-3-methyl morpholine. The title compound was obtained as a white solid with a yield of 35%.

MS (ESI): m/z, 480[M+H]$^+$.

Example 17: Preparation of (5-(2,4-di((2S,6R)-2,6-dimethyl)pyrido[4,3-d]pyrimidin-7-yl)-2-methoxyphenyl)methanol (Compound 17)

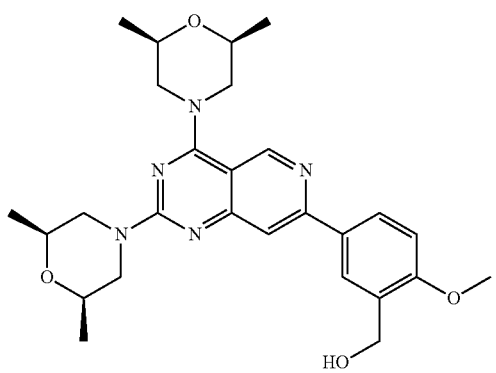

The title compound was prepared in the same manner as that in Example 13, and steps b, c, and e were the same as those in Example 13, except that morpholine in steps a and d was replaced with (2S,6R)-2,6-dimethyl morpholine. The title compound was obtained as a white solid with a yield of 55%.

MS (ESI): m/z, 494[M+H]$^+$.

Example 18: Preparation of (5-(2,4-di((S)-3-methylmorpholinyl)pyrido[4,3-d]pyrimidin-7-yl)-2-methoxyphenyl)methanol (Compound 18)

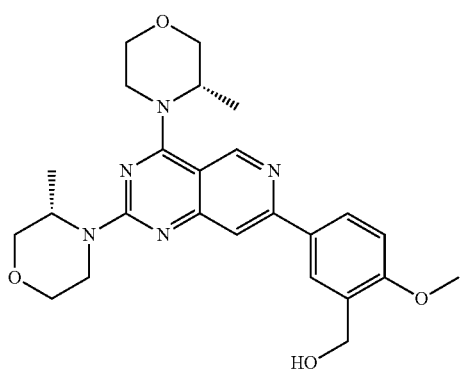

The title compound was prepared in the same manner as that in Example 13, and steps b, c, and e were the same as those in Example 13, except that morpholine in steps a and d were replaced with (S)-3-methyl morpholine. The title compound was obtained as a white solid with a yield of 56%.

MS (ESI): m/z, 466[M+H]$^+$.

Example 19: Preparation of (S)-(2-methoxy-5-(4-(3-methylmorpholinyl)-2-morpholinylpyrido[4,3-d]pyrimidin-7-yl)phenyl)methanol (Compound 19)

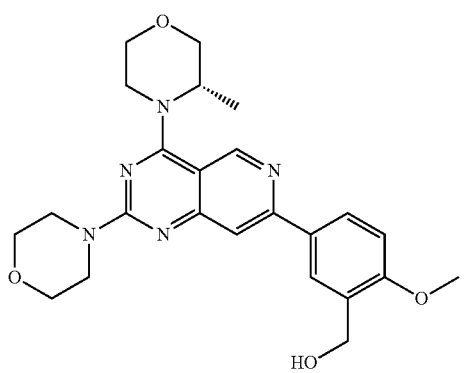

The title compound was prepared in the same manner as that in Example 13, and steps b, c, d and e were the same as those in Example 13, except that morpholine in step a was replaced with (S)-3-methyl morpholine. The title compound was obtained as a white solid with a yield of 30%.

MS (ESI): m/z, 452[M+H]$^+$.

Example 20: Preparation of (5-(2,4-di(8-oxa-3-azabicyclo[3.2.1]octan-3-yl)pyrido[4,3-d]pyrimidin-7-yl)-2-methoxyphenyl)methanol (Compound 20)

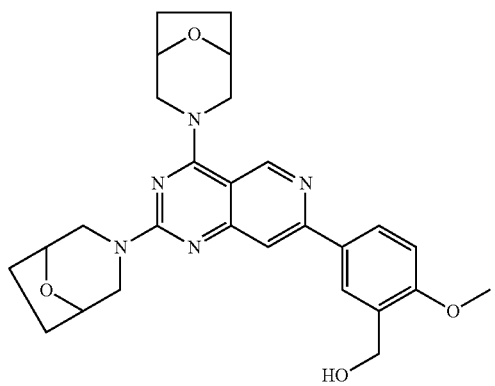

The title compound was prepared in the same manner as that in Example 13, and steps b, c and e were the same as those in Example 13, except that morpholine in steps a and d were replaced with 8-oxa-3-azabicyclo[3.2.1]octane hydrochloride. The title compound was obtained as a yellow solid with a yield of 45%.

MS (ESI): m/z, 490[M+H]$^+$.

Example 21: Preparation of (5-(4-(8-oxa-3-azabicyclo[3.2.1]octan-3-yl)-2-morpholinylpyrido[4,3-d]pyrimidin-7-yl)-2-methoxyphenyl)methanol (Compound 21)

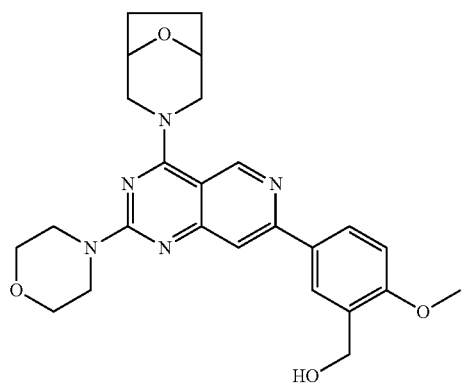

The title compound was prepared in the same manner as that in Example 13, and steps b, c, d and e were the same as those in Example 13, except that morpholine in step a was replaced with 8-oxa-3-azabicyclo[3.2.1]octane hydrochloride. The title compound was obtained as a white solid with a yield of 35%.

MS (ESI): m/z, 464[M+H]$^+$.

Example 22: Preparation of (5-(4-(8-oxa-3-azabicyclo[3.2.1]octan-3-yl)-2-((S)-3-methylmorpholinyl)pyrido[4,3-d]pyrimidin-7-yl)-2-methoxyphenyl)methanol (Compound 22)

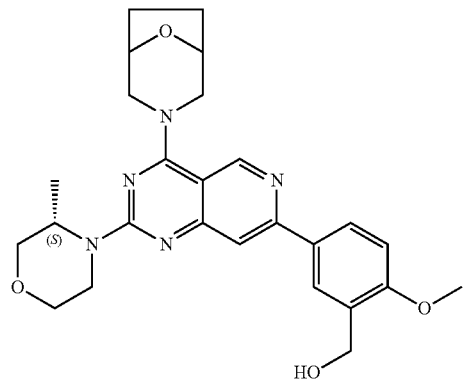

The title compound was prepared in the same manner as that in Example 13, and steps b, c and e were the same as those in Example 13, except that morpholine in step a was replace with 8-oxa-3-azabicyclo[3.2.1]octane hydrochloride, and morpholine in step d was replaced with (S)-3-methylmorpholine. The title compound was obtained as a yellow solid with a yield of 35%.

MS (ESI): m/z, 478[M+H]$^+$.

Example 23: Preparation of (5-(2,4-di(3-oxa-8-azabicyclo[3.2.1]octan-8-yl)pyrido[4,3-d]pyrimidin-7-yl)-2-methoxyphenyl)methanol (Compound 23)

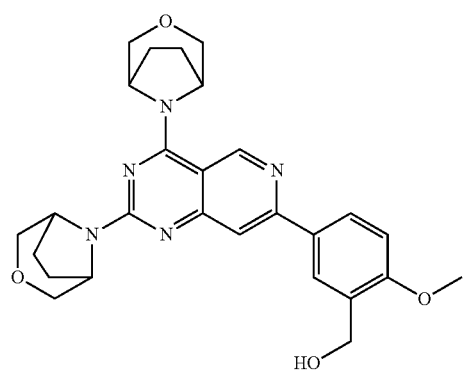

The title compound was prepared in the same manner as that in Example 13, and steps b, c and e were the same as those in Example 13, except that morpholine in steps a and d were replaced with 3-oxa-8-azabicyclo[3.2.1]octane hydrochloride. The title compound was obtained as a white solid with a yield of 50%.

MS (ESI): m/z, 490[M+H]$^+$.

Example 24: Preparation of (5-(4-(1R,5S)-3-oxa-8-azabicyclo[3.2.1]octan-8-yl)-2-morpholinylpyrido[4,3-d]pyrimidin-7-yl)-2-methoxyphenyl)methanol (Compound 24)

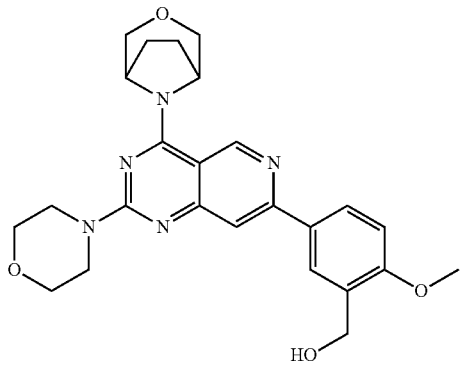

The title compound was prepared in the same manner as that in Example 13, and steps b, c, d and e were the same as those in Example 13, except that morpholine in step a was replaced with 3-oxa-8-azabicyclo[3.2.1]octane hydrochloride. The title compound was obtained as a white solid with a yield of 35%.

MS (ESI): m/z, 464[M+H]$^+$.

Example 25: Preparation of (5-(4-((1R,5S)-3-oxa-8-azabicyclo[3.2.1]octan-8-yl)-2-((S)-3-methylmorpholinyl)pyrido[4,3-d]pyrimidin-7-yl)-2-methoxyphenyl)methanol (Compound 25)

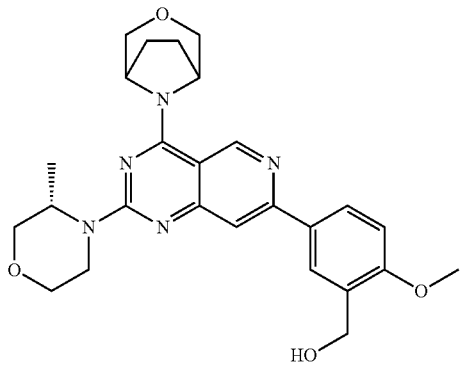

The title compound was prepared in the same manner as that in Example 13, and steps b, c and e were the same as those in Example 13, except that morpholine in step a was replace with 3-oxa-3-azabicyclo[3.2.1]octane hydrochloride, and morpholine in step d was replaced with (S)-8-methylmorpholine. The title compound was obtained as a yellow solid with a yield of 35%.

MS (ESI): m/z, 478[M+H]$^+$.

Example 26: Preparation of (4,4'-(7-phenylpyrido[4,3-d]pyrimidin-2,4-diyl)-dimorpholine) (Compound 26)

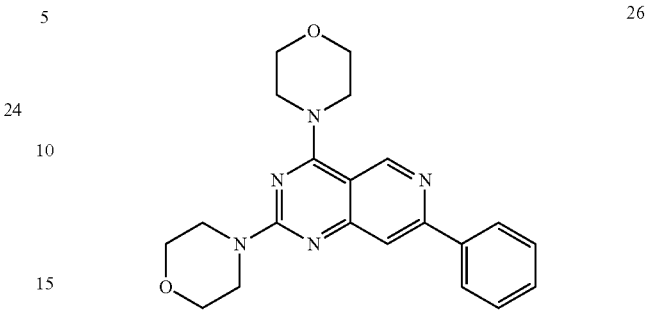

The title compound was prepared in the same manner as that in Example 13, and steps a, c, d and e were the same as those in Example 13, except that 5-acetenyl-2-methoxybenzyl pivalate in step b was replaced with phenylacetylene. The title compound was obtained with a yield of 52%.

MS (ESI): m/z, 378[M+H]$^+$.

Example 27: Preparation of (S)-3-methyl-4-(4-morpholinyl-7-phenylpyrido[4,3-d]pyrimidin-2-yl)morpholine) (Compound 27)

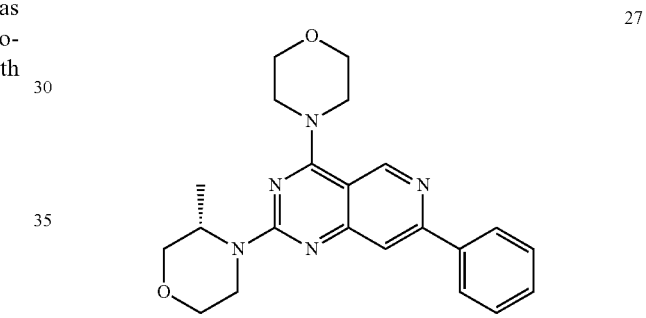

The title compound was prepared in the same manner as that in Example 13, and steps a, c and e were the same as those in Example 13, except that 5-acetenyl-2-methoxybenzyl pivalate in step b was replaced with phenylacetylene and morpholine in step d was replaced with (S)-3-methyl morpholine. The title compound was obtained with a yield of 42%.

MS (ESI): m/z, 391[M+H]$^+$.

Example 28: Preparation of 3-(4-morpholinyl-7-phenylpyrido[4,3-d]pyrimidin-2-yl)-8-oxa-3-azabicyclo[3.2.1]octane (Compound 28)

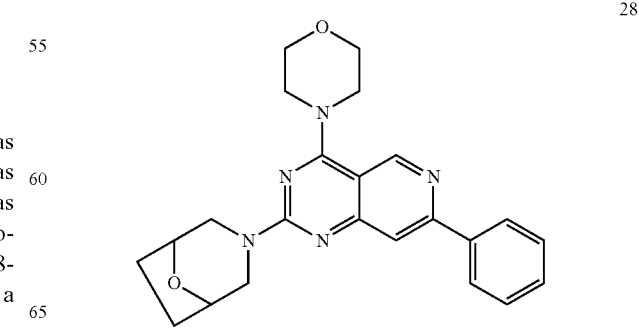

The title compound was prepared in the same manner as that in Example 13, and steps a, c and e were the same as those in Example 13, except that 5-acetenyl-2-methoxybenzyl pivalate in step b was replaced with phenylacetylene and morpholine in step d was replaced with 8-oxa-3-azadicyclo[3.2.1]octane hydrochloride. The title compound was obtained with a yield of 42%.

MS (ESI): m/z, 404[M+H]+.

Example 29: Preparation of (S)-3-methyl-4-(2-morpholinyl-7-phenylpyrido[4,3-d]pyrimidin-4-yl)morpholine (Compound 29)

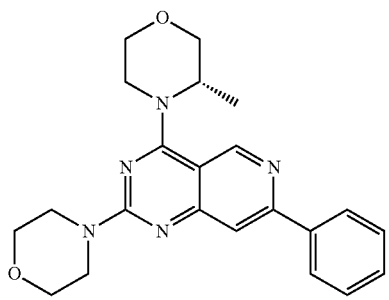

29

The title compound was prepared in the same manner as that in Example 13, and steps c, d and e were the same as those in Example 13, except that 5-acetenyl-2-methoxybenzyl pivalate in step b was replaced with phenylacetylene and morpholine in step a was replaced with (S)-3-methyl morpholine. The title compound was obtained with a yield of 42%.

MS (ESI): m/z, 392[M+H]+.

Example 30: Preparation of (3S,3'S)-4,4'-(7-phenylpyrido[4,3-d]pyrimidin-2,4-diyl)-di(3-methylmorpholine) (Compound 30)

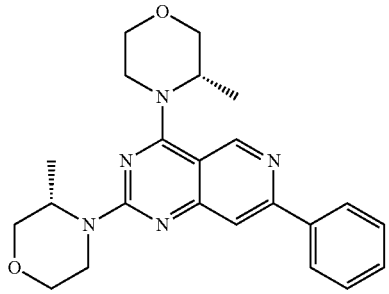

30

The title compound was prepared in the same manner as that in Example 13, and steps c and e were the same as those in Example 13, except that 5-acetenyl-2-methoxybenzyl pivalate in step b was replaced with phenylacetylene and morpholine in steps a and d were replaced with (S)-3-methyl morpholine. The title compound was obtained with a yield of 42%.

MS (ESI): m/z, 406[M+H]+.

Example 31: Preparation of 3-(4-((S)-3-methylmorpholinyl)-7-phenylpyrido[4,3-d]pyrimidin-2-yl)-8-oxa-3-azabicyclo[3.2.1]octane (Compound 31)

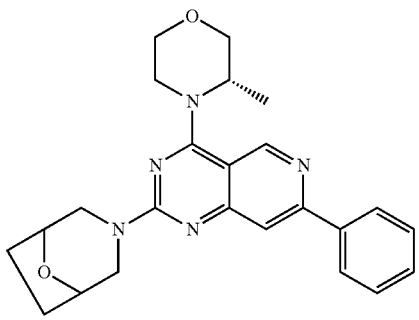

31

The title compound was prepared in the same manner as that in Example 13, and steps c and e were the same as those in Example 13, except that 5-acetenyl-2-methoxybenzyl pivalate in step b was replaced with phenylacetylene, morpholine in step a was replaced with (S)-3-methyl morpholine and morpholine in step d was replaced with 8-oxa-3-azadicyclo[3.2.1]octane hydrochloride. The title compound was obtained with a yield of 52%.

MS (ESI): m/z, 418[M+H]+.

Example 32: Preparation of 4,4'-(7-phenylpyrimido[4,5-d]pyrimidin-2,4-diyl)-dimorpholine (Compound 32)

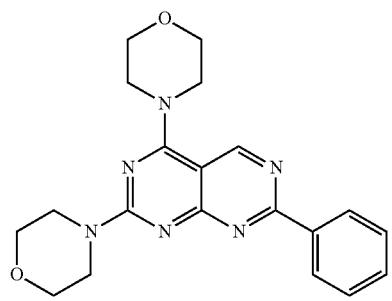

32

The reaction scheme was as follows:

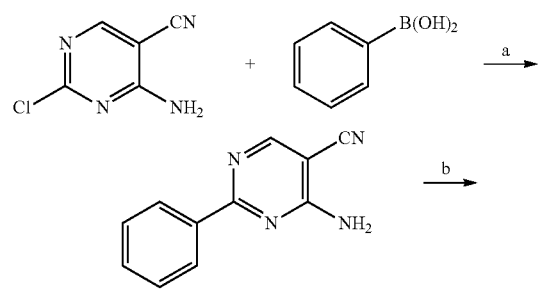

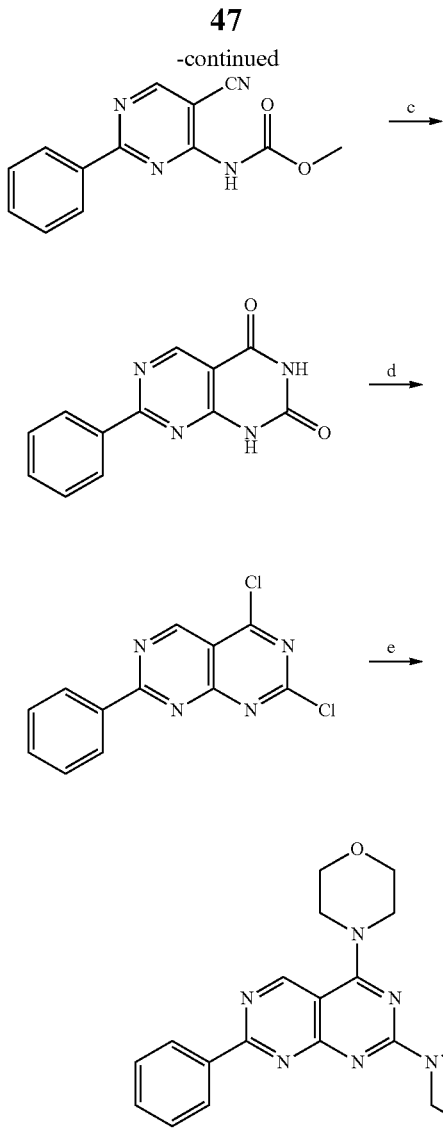

Reagents and conditions: a) potassium phosphate, palladium acetate, 1,1'-bis(di-t-butylphosphino)ferrocenepalladium dichloride, dioxane, reflux; b) methyl chloroformate, sodium hydride, tetrahydrofuran, room temperature; c) 30 wt % hydrogen peroxide, sodium hydroxide, ethanol, reflux; d) phosphorus oxychloride, N,N-diisopropylethylamine, reflux; e) morpholine, N,N-diisopropylethylamine, tetrahydrofuran, room temperature.

a) 4-amino-2-phenylpyrimidine-5-carbonitrile

To 4-amino-2-chloropyrimidine-5-carbonitrile (1 g, 6.47 mmol), 30 mL of dioxane, phenylboronic acid (1.2 g, 9.70 mmol), potassium phosphate (2.7 g, 12.94 mmol), palladium acetate (72.5 mg, 0.32 mmol) and 1,1'-bis(di-t-butyl phosphino) ferrocene palladium dichloride (153 mg, 0.32 mmol) were added. The resultant mixture was degassed with argon three times, refluxed overnight, cooled to room temperature, and directly loaded on a silica gel column eluting with petroleum ether/ethyl acetate (V/V=8:1) to give 500 mg of the title compound as a white solid with a yield of 42%.

MS: m/z, 197[M+H]$^+$.

b) methyl 5-cyano-2-phenylpyrimidin-4-ylcarbamate

Sodium hydride (350 mg, 14.3 mmol) was suspended in 60 mL of tetrahydrofuran. 4-amino-2-phenylpyrimidine-5-carbonitrile (1 g, 5.09 mmol) obtained as above dissolved in 40 mL of tetrahydrofuran was added dropwisely into the sodium hydride solution under ice bath, reacted at room temperature for 3 hours, and added dropwisely with methyl chloroformate (722 mg, 7.65 mmol), and further reacted overnight. After the solvent was removed under reduced pressure, the resultant mixture was added with water, extracted with ethyl acetate, dried over anhydrous over sodium sulfate, and concentrated under reduced pressure. The residue was purified by flash column chromatography on silica gel by eluting with petroleum ether/ethyl acetate (V/V=4:1) to give 1 g of the title compound as a white solid with a yield of 78%.

MS (ESI): m/z, 255[M+H]$^+$.

c) 7-phenyl-pyrimido[4,5-d]pyrimidine-2,4(1H,3H)-dione

To methyl 5-cyano-2-phenylpyrimidin-4-ylcarbamate (100 mg, 0.39 mmol), 8 mL of ethanol, 30 mg of sodium hydroxide and 2 mL of a 30 wt % the peroxide hydrogen were added. The mixture was refluxed for 2 hours, added with 8 mL of water, concentrated under reduced pressure, and filtered to give a white solid, which was washed with water three times to give 30 mg of the title compound as a white solid with a yield of 32%.

MS (ESI): m/z, 241[M+H]$^+$.

d) 2,4-dichloro-7-phenylpyrimido[4,5-d]pyrimidine

To 7-phenylpyrimido[4,5-d]pyrimidine-2,4(1H,3H)-dione (30 mg, 0.13 mmol), 2 mL of phosphorus oxychloride and N,N-diisopropylethylamine (18 mg, 0.14 mmol) were added thereto. The mixture was refluxed overnight, cooled to room temperature, poured onto crushed ice, neutralized with saturated aqueous solution of sodium carbonate to a pH of 7-8, and extracted with dichloromethane. The organic phase was washed with saturated sodium bicarbonate solution and saturated brine in sequence, dried over anhydrous sodium sulfate, and concentrated under reduced pressure to give 32 mg of the title compound as a tan solid with a yield of 92%. The product was used directly in the next step without further purification.

e) 4,4'-(7-phenylpyrimido[4,5-d]pyrimidine-2,4-diyl)dimorpholine 2,4-dichloro-7-phenylpyrimido[4,5-d]pyrimidine (32 mg, 0.16 mmol) was dissolved in 2 mL of tetrahydrofuran, added with N,N-diisopropylethylamine (35 mg, 0.27 mmol) and morpholine (50 mg, 0.57 mmol), and reacted at room temperature overnight. After the solvent was removed under reduced pressure, the mixture was added with water and extracted with ethyl acetate. The organic phase was dried over anhydrous sodium sulfate, and concentrated under reduced pressure. The residue was purified by flash silica gel column chromatography eluting with petroleum ether/ethyl acetate (V/V=2:1) to give 21 mg of the title compound as a yellow solid with a yield of 49%.

MS (ESI): m/z, 379[M+H]$^+$.

Example 33: Preparation of (3S,3'S)-4,4'-(7-phenyl pyrimido[4,5-d]pyrimidin-2,4-diyl)-di(3-methyl morpholine) (Compound 33)

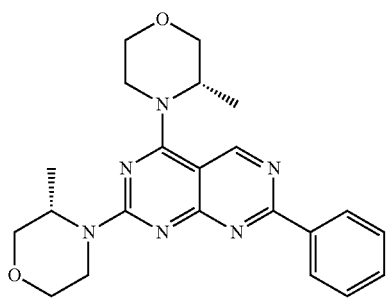

33

The title compound was prepared in the same manner as that in Example 32, and steps a, b, c and d were the same as those in Example 32, except that morpholine in step e was replaced with (S)-3-methyl morpholine. The title compound was obtained with a yield of 66%.

MS (ESI): m/z, 407[M+H]$^+$.

Example 34: Preparation of 3,3'-(7-phenylpyrimido [4,5-d]pyrimidin-2,4-diyl)-di(8-oxa-3-azabicyclo [3.2.1]octane) (Compound 34)

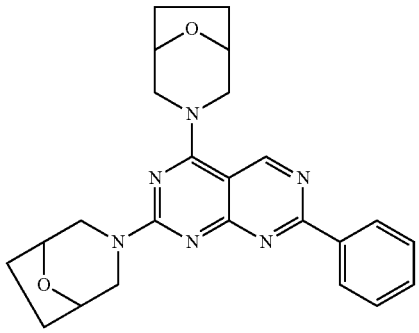

34

The title compound was prepared in the same manner as that in Example 32, and steps a, b, c and d were the same as those in Example 32, except that morpholine in step e was replaced with 8-oxa-3-azabicyclo[3.2.1]octane hydrochloride. The title compound was obtained with a yield of 64%.

MS (ESI): m/z, 431[M+H]$^+$.

Example 35: Preparation of 3-(2,4-di(3-oxa-8-azabicyclo[3.2.1]octan-8-yl)pyrido[2,3-d]pyrimidin-7-yl)-N-methylbenzamide (Compound 35)

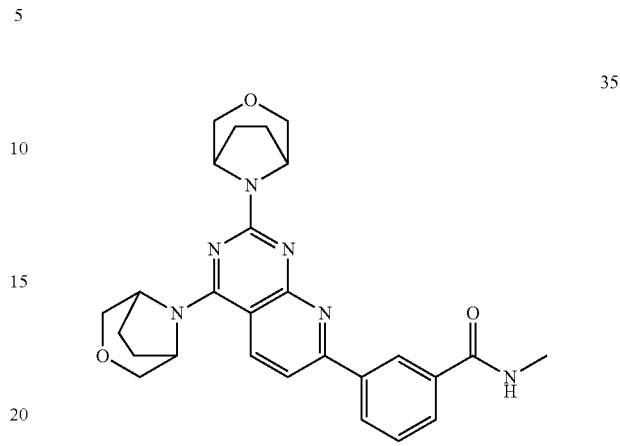

35

The reaction scheme was as follows:

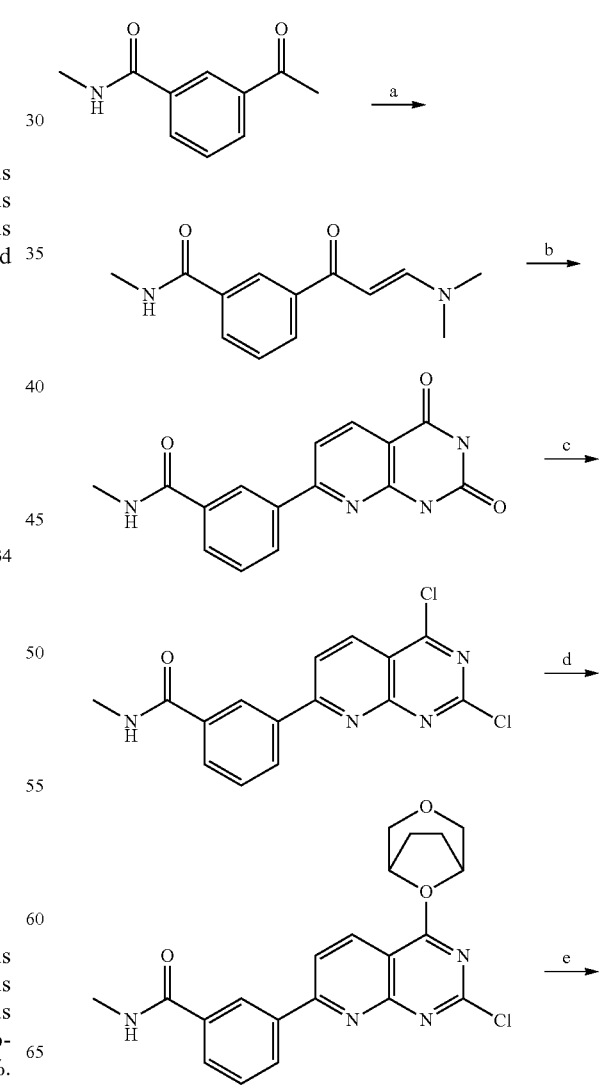

-continued

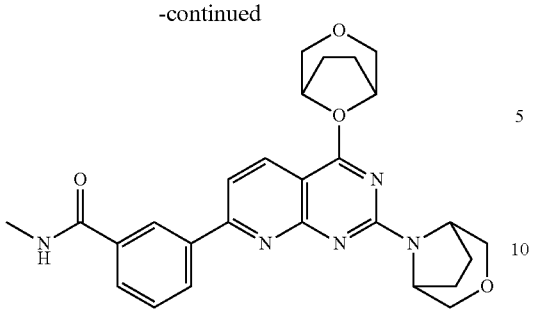

Reagents and conditions: a) N,N-dimethylformamide dimethyl acetal, toluene, reflux; b) 6-aminouracil, glacial acetic acid, water, dimethylsulfoxide, 99° C.; c) phosphorus oxychloride, N,N-diisopropylethylamine, anisole, 80° C.; d) 3-oxa-8-azabicyclo[3.2.1]octane hydrochloride, N,N-diisopropylethylamine, tetrahydrofuran, room temperature; e) 3-oxa-8-azabicyclo[3.2.1]octane hydrochloride, N,N-diisopropylethylamine, isopropanol, microwave at 160° C., 80 min.

a) 3-formamidoacetophenone and N,N-dimethylformamide dimethyl acetal were subjected to a condensation reaction to obtain (E)-3-(3-(dimethylamino)acryl)-N-methyl benzamide; b) (E)-3-(3-(dimethylamino)acryl)-N-methylbenzamide and 6-aminouracil were subjected to a condensation reaction to give 3-(2,4-dioxo-1,2,3,4-tetrahydropyrido[2,3-d]pyrimidin-yl)-N-benzamide; c) 3-(2,4-dioxo-1,2,3,4-tetrahydropyrido[2,3-d]pyrimidin-yl)-N-benzamide was reacted in the presence of phosphorus oxychloride to give a dichlorinated intermediate; d) and e) the dichlorinated intermediate was subjected to a substitution reaction with 3-oxa-8-azabicyclo[3.2.1]octane hydrochloride successively to give the title compound with a yield of 64%.

MS (ESI): m/z, 487[M+H]$^+$.

Example 36: Preparation of 3-(2,4-di(8-oxa-3-azabicyclo[3.2.1]octan-3-yl)pyrido[2,3-d]pyrimidin-7-yl)-N-methylbenzamide (Compound 36)

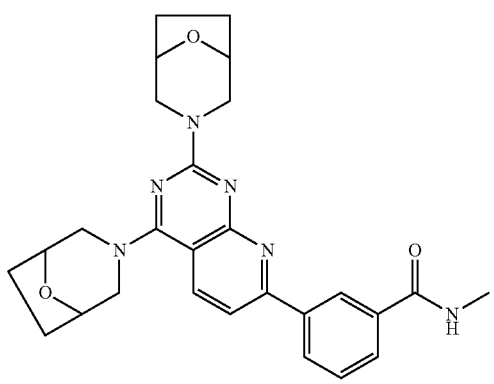

The title compound was prepared in the same manner as that in Example 35, and steps a, b, and c were the same as those in Example 35, except that 3-oxa-8-azabicyclo[3.2.35]octane hydrochloride in steps d and e were replaced with 8-oxa-3-azabicyclo[3.2.1]octane hydrochloride. The title compound was obtained with a yield of 64%.

MS (ESI): m/z, 487[M+H]$^+$.

Example 37: Preparation of 3-(2-(3-oxa-8-azabicyclo[3.2.1]octan-8-yl)-4-((S)-3-methylmorpholinyl)pyrido[2,3-d]pyrimidin-7-yl)-N-methylbenzamide (Compound 37)

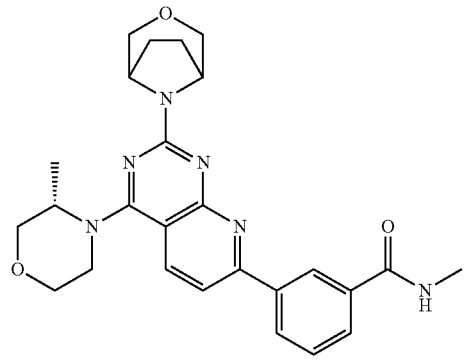

The title compound was prepared in the same manner as that in Example 35, and steps a, b, c, and e were the same as those in Example 35, except that 3-oxa-8-azabicyclo[3.2.1]octane hydrochloride in step d was replaced with (S)-3-methylmorpholine. The title compound was obtained with a yield of 64%.

MS (ESI): m/z, 475[M+H]$^+$.

Example 38: Preparation of 3-(2-(8-oxa-3-azabicyclo[3.2.1]octan-3-yl)-4-((S)-3-methylmorpholinyl)pyrido[2,3-d]pyrimidin-7-yl)-N-methylbenzamide (Compound 38)

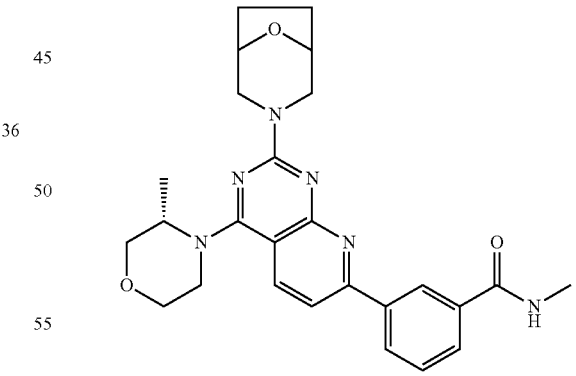

The title compound was prepared in the same manner as that in Example 35, and steps a, b, and c were the same as those in Example 35, except that 3-oxa-8-azabicyclo[3.2.1] octane hydrochloride in step d was replaced with (S)-3-methylmorpholine, and 3-oxa-8-azabicyclo[3.2.1]octane hydrochloride in step e was replaced with 8-oxa-3-azabicyclo[3.2.1]octane hydrochloride. The title compound was obtained with a yield of 64%.

MS (ESI): m/z, 475[M+H]$^+$.

Example 39: Preparation of 3-(2-(3-oxa-8-azabicyclo[3.2.1]octan-8-yl)-4-morpholinylpyrido[2,3-d]pyrimidin-7-yl)-N-methylbenzamide (Compound 39)

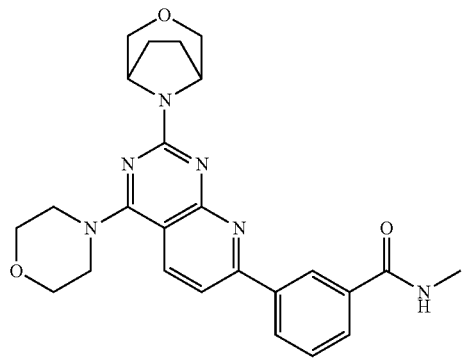

The title compound was prepared in the same manner as that in Example 35, and steps a, b, c, d, and e were the same as those in Example 35, except that 3-oxa-8-azabicyclo[3.2.1]octane hydrochloride in step d was replaced with morpholine. The title compound was obtained with a yield of 60%.

MS (ESI): m/z, 461[M+H]$^+$.

Example 40: Preparation of 3-(2-(8-oxa-3-azabicyclo[3.2.1]octan-3-yl)-4-morpholinylpyrido[2,3-d]pyrimidin-7-yl)-N-methylbenzamide (Compound 40)

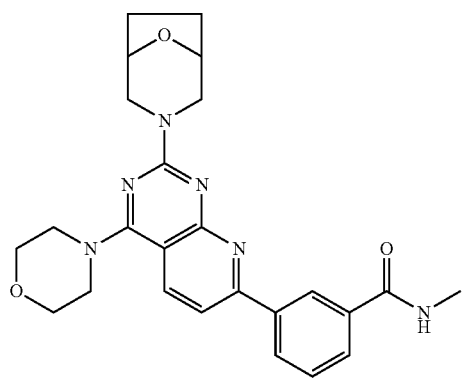

The title compound was prepared in the same manner as that in Example 35, and steps a, b, and c were the same as those in Example 35, Except that 3-oxa-8-azabicyclo[3.2.1]octane hydrochloride in step d was replaced with morpholine, and 3-oxa-8-azabicyclo[3.2.1]octane hydrochloride in step e was replaced with 8-oxa-3-azabicyclo[3.2.1]octane hydrochloride. The title compound was obtained with a yield of 60%.

MS (ESI): m/z, 461[M+H]$^+$.

Example 41: Preparation of 3-(2-(3-oxa-8-azabicyclo[3.2.1]octan-8-yl)-4-((2S,6R)-2,6-dimethylmorpholinyl)pyrido[2,3-d]pyrimidin-7-yl)-N-methylbenzamide (Compound 41)

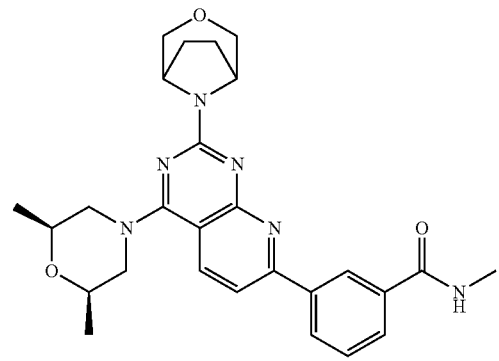

The title compound was prepared in the same manner as that in Example 35, and steps a, b, c and e were the same as those in Example 35, except that 3-oxa-8-azabicyclo[3.2.1]octane hydrochloride in step d was replaced with (2S,6R)-2,6-dimethyl morpholine. The title compound was obtained with a yield of 64%.

MS (ESI): m/z, 489[M+H]$^+$.

Example 42: Preparation of 3-(2-(8-oxa-3-azabicyclo[3.2.1]octan-8-yl)-4-((2S,6R)-2,6-dimethylmorpholinyl)pyrido[2,3-d]pyrimidin-7-yl)-N-methylbenzamide (Compound 42)

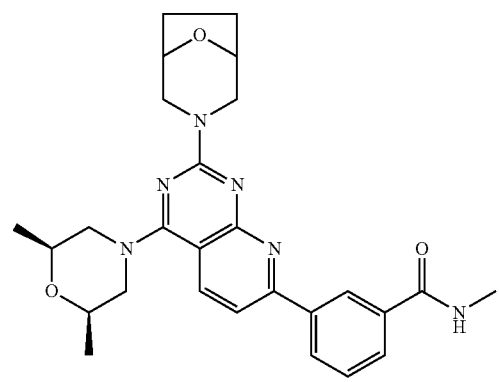

The title compound was prepared in the same manner as that in Example 35, and steps a, b, and c were the same as those in Example 35, except that 3-oxa-8-azabicyclo[3.2.1]octane hydrochloride in step d was replaced with (2S,6R)-2,6-dimethyl morpholine, and 3-oxa-8-azabicyclo[3.2.1]octane hydrochloride in step e was replaced with 8-oxa-3-azabicyclo[3.2.1]octane hydrochloride. The title compound was obtained with a yield of 66%.

MS (ESI): m/z, 489[M+H]$^+$.

Example 43: Preparation of 3-(4-(3-oxa-8-azabicyclo[3.2.1]octan-8-yl)-2-morpholinylpyrido[2,3-d]pyrimidin-7-yl)-N-methylbenzamide (Compound 43)

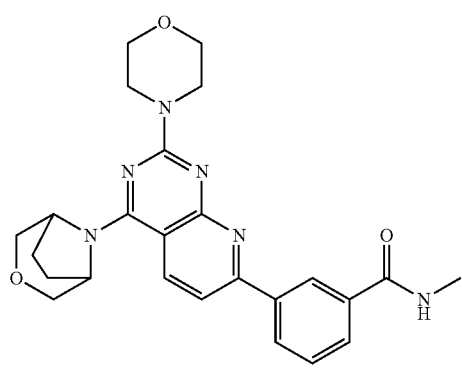

The title compound was prepared in the same manner as that in Example 35, and steps a, b, c, and d were the same as those in Example 35, except that 3-oxa-8-azabicyclo[3.2.1]octane hydrochloride in step e was replaced with morpholine. The title compound was obtained with a yield of 64%.

MS (ESI): m/z, 461[M+H]$^+$.

Example 44: Preparation of 3-(4-(3-oxa-8-azabicyclo[3.2.1]octan-8-yl)-2-((S)-3-methylmorpholinyl)pyrido[2,3-d]pyrimidin-7-yl)-N-methylbenzamide (Compound 44)

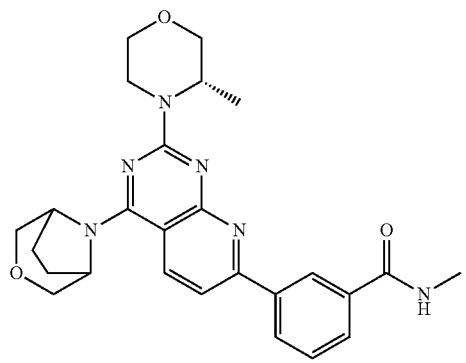

The title compound was prepared in the same manner as that in Example 35, and steps a, b, c, and d were the same as those in Example 35, except that 3-oxa-8-azabicyclo[3.2.1]octane hydrochloride in step e was replaced with (S)-3-methylmorpholine. The title compound was obtained with a yield of 64%.

MS (ESI): m/z, 475[M+H]$^+$.

Example 45: Preparation of 3-(4-(3-oxa-8-azabicyclo[3.2.1]octan-8-yl)-2-((2S,6R)-2,6-dimethylmorpholinyl)pyrido[2,3-d]pyrimidin-7-yl)-N-methylbenzamide (Compound 45)

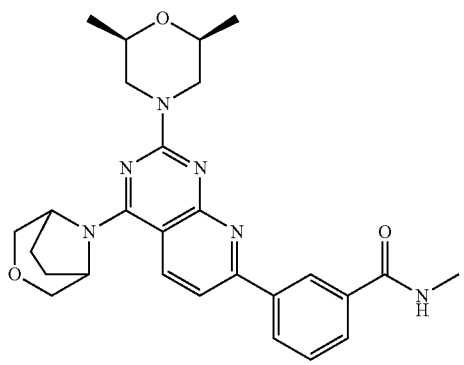

The title compound was prepared in the same manner as that in Example 35, and steps a, b, c and e were the same as those in Example 35, except that 3-oxa-8-azabicyclo[3.2.1]octane hydrochloride in step e was replaced with (2S,6R)-2,6-dimethylmorpholine. The title compound was obtained with a yield of 66%.

MS (ESI): m/z, 489[M+H]$^+$.

Example 46: Preparation of 3-(4-(3-oxa-8-azabicyclo[3.2.1]octan-8-yl)-2-((2-methoxyethyl)methylamino)pyrido[2,3-d]pyrimidin-7-yl)-N-methylbenzamide (Compound 46)

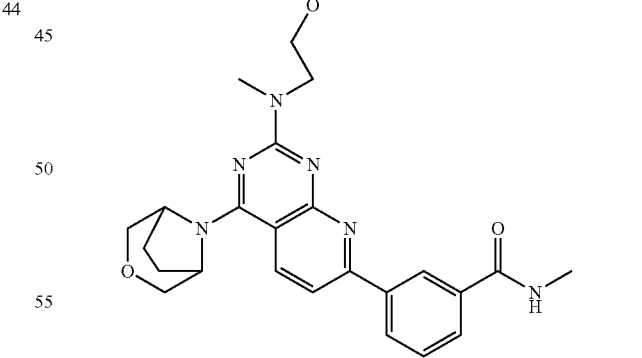

The title compound was prepared in the same manner as that in Example 35, and steps a, b, c and d were the same as those in Example 35, except that 3-oxa-8-azabicyclo[3.2.1]octane hydrochloride in step e was replaced with 2-(methoxyethyl)methylamine. The title compound was obtained with a yield of 60%.

MS (ESI): m/z, 463[M+H]$^+$.

Example 47: Preparation of 3-(2-(8-oxa-3-azabicyclo[3.2.1]octan-3-yl)-4-((3-oxa-8-azabicyclo[3.2.1]octan-8-yl)pyrido[2,3-d]pyrimidin-7-yl)-N-methylbenzamide (Compound 47)

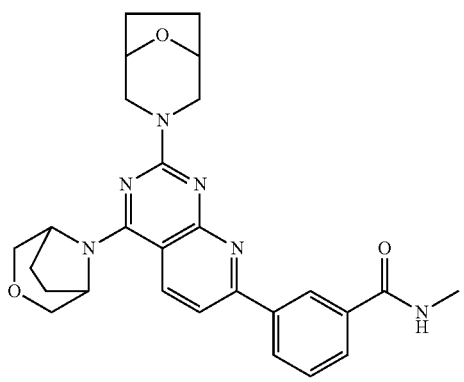

The title compound was prepared in the same manner as that in Example 35, and steps a, b, c and d were the same as those in Example 35, except that 3-oxa-8-azabicyclo[3.2.1]octane hydrochloride in step e was replaced with 8-oxa-3-azabicyclo[3.2.1]octane hydrochloride. The title compound was obtained with a yield of 60%.

MS (ESI): m/z, 487[M+H]$^+$.

Example 48: Preparation of 3-(4-(8-oxa-3-azabicyclo[3.2.1]octan-3-yl)-2-morpholinylpyrido[2,3-d]pyrimidin-7-yl)-N-methylbenzamide (Compound 48)

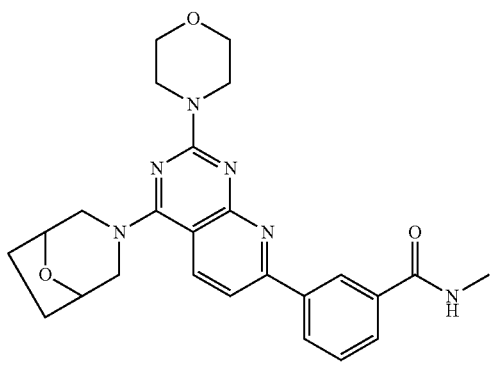

The title compound was prepared in the same manner as that in Example 35, and steps a, b, and c were the same as those in Example 35, except that 3-oxa-8-azabicyclo[3.2.1]octane hydrochloride in step d was replaced with 8-oxa-3-azabicyclo[3.2.1]octane hydrochloride, and 3-oxa-8-azabicyclo[3.2.1]octane hydrochloride in step e was replaced with morpholine. The title compound was obtained with a yield of 64%.

MS (ESI): m/z, 461[M+H]$^+$.

Example 49: Preparation of 3-(4-(8-oxa-3-azabicyclo[3.2.1]octan-3-yl)-2-((S)-3-methylmorpholinyl)pyrido[2,3-d]pyrimidin-7-yl)-N-methylbenzamide (Compound 49)

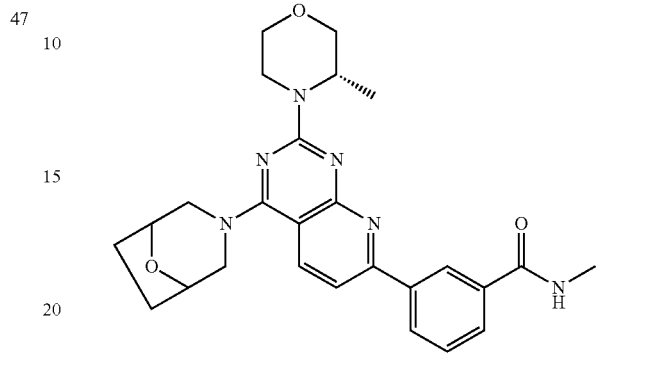

The title compound was prepared in the same manner as that in Example 35, and steps a, b, and c were the same as those in Example 35, except that 3-oxa-8-azabicyclo[3.2.1]octane hydrochloride in step d was replaced with 8-oxa-3-azabicyclo[3.2.1]octane hydrochloride, and 3-oxa-8-azabicyclo[3.2.1]octane hydrochloride in step e was replaced with (S)-3-methyl morpholine. The title compound was obtained with a yield of 64%.

MS (ESI): m/z, 475[M+H]$^+$.

Example 50: Preparation of 3-(4-(8-oxa-3-azabicyclo[3.2.1]octan-8-yl)-2-((2S,6R)-2,6-dimethylmorpholinyl)pyrido[2,3-d]pyrimidin-7-yl)-N-methylbenzamide (Compound 50)

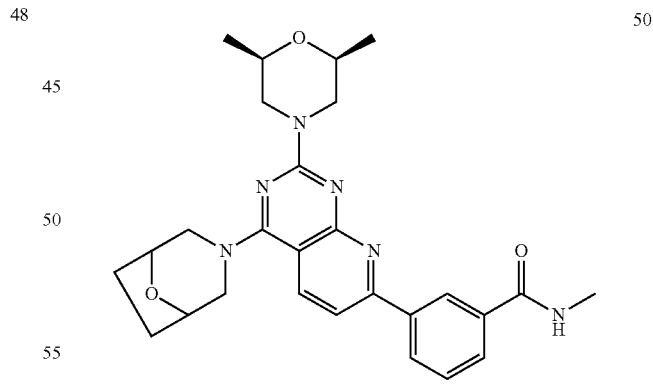

The title compound was prepared in the same manner as that in Example 35, and steps a, b and c were the same as those in Example 35, except that 3-oxa-8-azabicyclo[3.2.1]octane hydrochloride in step d was replaced with 8-oxa-3-azabicyclo[3.2.1]octane hydrochloride, and 3-oxa-8-azabicyclo[3.2.1]octane hydrochloride in step e was replaced with (2S,6R)-2,6-dimethyl morpholine. The title compound was obtained with a yield of 64%.

MS (ESI): m/z, 489[M+H]$^+$.

Example 51: Preparation of 3-(4-(8-oxa-3-azabicyclo[3.2.1]octan-3-yl)-2-((2-methoxyethyl)methylamino)pyrido[2,3-d]pyrimidin-7-yl)-N-methylbenzamide (Compound 51)

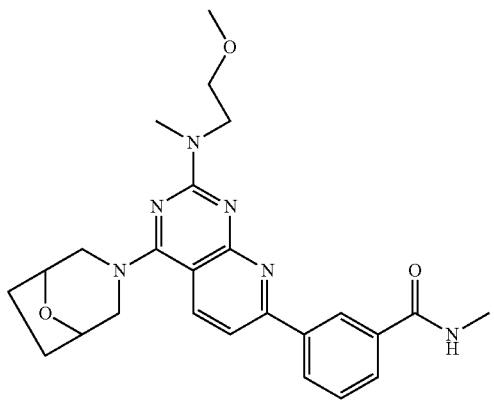

The title compound was prepared in the same manner as that in Example 35, and steps a, b and c were the same as those in Example 35, except that 3-oxa-8-azabicyclo[3.2.1]octane hydrochloride in step d was replaced with 8-oxa-3-azabicyclo[3.2.1]octane hydrochloride, and 3-oxa-8-azabicyclo[3.2.1]octane hydrochloride in step e was replaced with (2-methoxyethyl)methylamine. The title compound was obtained with a yield of 60%.

MS (ESI): m/z, 463[M+H]$^+$.

Example 52: Preparation of 3-(2-(3-oxa-8-azabicyclo[3.2.1]octan-8-yl)-4-((8-oxa-3-azabicyclo[3.2.1]octan-3-yl)pyrido[2,3-d]pyrimidin-7-yl)-N-methylbenzamide (Compound 52)

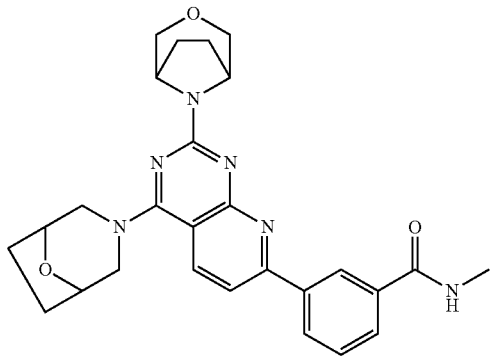

The title compound was prepared in the same manner as that in Example 35, and steps a, b, c and e were the same as those in Example 35, except that 3-oxa-8-azabicyclo[3.2.1]octane hydrochloride in step d was replaced with 8-oxa-3-azabicyclo[3.2.1]octane hydrochloride. The title compound was obtained with a yield of 66%.

MS (ESI): m/z, 487[M+H]$^+$.

Pharmacological Experiment Materials and Methods mTOR Kinase Test

The test on activity against mTOR Kinase was performed using a 1.7 nM mTOR (Millipore, 14-770M), a 50 nM ULight-4EBP1 (Perkin-Elmer, TRF0128M) and a 100 µM ATP on a detection system LANCE® Ultra (PerkinElmer). The compound was first prepared into a 20 mM stock solution, and then gradiently diluted so as to be added into the mTOR enzyme reaction system on a 384 well plates. The test concentrations were 20, 4, 0.8, 0.16, 0.032, 0.0064, 0.00128, 0.000256 µM (n=3). After the mTOR enzyme reaction was performed for 1.5 hours, it was terminated, and LANCE® Ultra systeme (PerkinElmer) was used to perform the test for 1 hour. The test results were recorded on a multimode microplate reader Synergy II (BioTek). Relative activity against mTOR %=(Lance light value of the well with drug−light value of the blank group (without mTOR)/ (light value of the DMSO group−light value of the blank group)×100%. The experimental data was processed with Microsoft Office Excel and Graphpad PRISM 5 to calculate IC$_{50}$. mTOR inhibition ratio was expressed by Mean±SD. The test results were shown in Table 1.

TABLE 1

Biological activity results obtained from mTOR Kinase test of the compounds prepared in respective Examples of present invention

| Compound | IC$_{50}$ (µM) |
| --- | --- |
| 1 | 0.001 |
| 2 | 0.003 |
| 3 | 0.003 |
| 4 | 0.005 |
| 5 | 0.005 |
| 6 | 0.022 |
| 7 | 0.004 |
| 8 | 0.002 |
| 9 | 0.011 |
| 10 | 4.872 |
| 11 | 0.009 |
| 12 | 0.057 |
| 13 | 0.451 |
| 14 | 0.062 |
| 15 | 0.297 |
| 16 | 1.633 |
| 17 | >20 |
| 18 | 0.012 |
| 19 | 0.071 |
| 20 | 0.080 |
| 21 | 0.205 |
| 22 | 0.073 |
| 23 | 0.035 |
| 24 | 0.035 |
| 25 | 0.018 |
| 26 | 0.464 |
| 27 | 0.134 |
| 28 | 0.435 |
| 29 | 0.153 |
| 30 | 0.058 |
| 31 | 0.074 |
| 32 | 1.701 |
| 33 | 0.413 |
| 34 | 0.195 |
| 35 | 0.060 |
| 37 | 0.021 |
| 38 | 0.032 |
| 43 | 0.166 |
| 44 | 0.039 |
| 45 | 0.093 |
| 49 | 0.064 |
| 52 | 0.071 |

Cell Proliferation Assay

Cell proliferation assay was based on two types of cell lines, i.e., human brain glioma U87MG and human prostate cancer LNCap, both of which were from ATCC. U87MG and LNCap contain PTEN gene deletion, and belongs to mTOR signal-dependent tumor cells. Cell culture media and related reagents were from GIBCO. U87MG cells were cultured in a MEM complete medium (containing 10% fetal bovine serum, 100 U/mL penicillin and 100 µg/mL streptomycin). LNCap cells were cultured in a RPMI-1640 complete medium (containing 10% fetal bovine serum, 100

U/mL penicillin and 100 μg/mL streptomycin). One day before the experiment, U87MG and LNCap cells in growth phase were enzymatically digested by trypsin to prepare a cell suspension added into a 96-well plate with 5×10³ cells per well (150 μL/well), and cultured in an incubator with 5% $CO_2$, at 37° C. to be adherent in the next day and ready for use. The stock solution (20 mM) was gradiently diluted with the medium as designed, added into the test cells with 50 μL/well, and the final concentrations were 60, 20, 6.67, 2.22, 0.74, 0.247, 0.0823, 0.027 μM (n=3). Cells/compound was cultured for 3 days, and MTS method was used to test cell proliferation. MTS and PMS were purchased from Sigma company, a stock solution of MTS/PMS (20:1) was added into the test cells with 20 μL/well. After a suitable time of incubation, the proliferation assay results was recorded on a 96 well plate microplate reader.

Relative cell viability %=($A_{490}$ value of administered group−light value of the blank group)/(light value of DMSO group−light value of blank group)×100%.

The experimental data were processed with Microsoft Office Excel and Graphpad PRISM 5 to calculate $IC_{50}$. Cellular proliferation inhibition rate was expressed by Mean±SD. The test results were shown in Table 2.

TABLE 2

Biological activity results of the compounds prepared in respective Examples of present invention obtained from the proliferation inhibition test of tumor cell:

| Compound | U87MG $IC_{50}$ (μM) | LNCap $IC_{50}$ (μM) |
| --- | --- | --- |
| 1 | 0.330 | <0.027 |
| 2 | 0.210 | 0.890 |
| 3 | 0.110 | <0.027 |
| 4 | 0.240 | 0.060 |
| 5 | 0.320 | 0.060 |
| 6 | 1.070 | 0.220 |
| 7 | 0.200 | 0.027 |
| 8 | 0.070 | <0.027 |
| 9 | 0.510 | 0.320 |
| 10 | 23.910 | >60 |
| 11 | 0.280 | 0.070 |
| 12 | 3.170 | 1.110 |
| 13 | >60 | 17.950 |
| 14 | 11.360 | 3.370 |
| 15 | 24.480 | 9.390 |
| 16 | >60 | >60 |
| 17 | >60 | 21.390 |
| 18 | 2.580 | 1.200 |
| 19 | 14.790 | 2.750 |
| 20 | 18.740 | 2.590 |
| 21 | 12.700 | 6.090 |
| 22 | 18.360 | 2.290 |
| 23 | >60 | >60 |
| 24 | 55.900 | >60 |
| 25 | 4.970 | 1.780 |
| 26 | 6.354 | 2.074 |
| 27 | 5.679 | 1.679 |
| 28 | 6.443 | 4.200 |
| 29 | 2.293 | 0.829 |
| 30 | 1.139 | 0.361 |
| 31 | 1.386 | 0.423 |
| 32 | 20.360 | 6.710 |
| 33 | 17.690 | 2.030 |
| 34 | 9.320 | 0.990 |
| 35 | 0.510 | 0.240 |
| 37 | 0.240 | 0.090 |
| 38 | 0.470 | 0.130 |
| 43 | 2.080 | 0.760 |
| 44 | 0.560 | 0.240 |
| 45 | 1.400 | 0.670 |
| 49 | 1.000 | 0.500 |
| 52 | 1.010 | 0.420 |

The compounds listed in Table 1 and Table 2 have a strong inhibitory activity against mTOR and a mTOR-dependent antitumor activity.

The above examples are merely for illustrative purposes, and the scope of the present invention is not limited thereto. Various modifications will be apparent to those skilled in the art, and the scope of the invention is only limited by the appended claims.

The invention claimed is:

1. A compound represented by formula (Ia), or the isomer, the pharmaceutically acceptable salt, the ester or the solvate thereof:

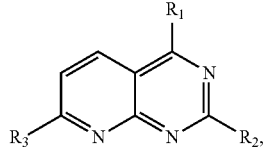

(Ia)

wherein $R_1$ and $R_2$ are each independently 3-oxa-8-azabicyclo[3.2.1]octanyl, 8-oxa-3-azabicyclo[3.2.1]octanyl, or $NR_AR_B$, and at least one of $R_1$ and $R_2$ is 3-oxa-8-azabicyclo[3.2.1]octanyl or 8-oxa-3-azabicyclo[3.2.1]octanyl;

wherein $R_A$ and $R_B$ are each independently H, C1-C6 alkyl unsubstituted or substituted by C1-C6 alkoxy or halogen, or C1-C6 alkoxy unsubstituted or substituted by halogen, or $R_A$ and $R_B$, together with N to which they are linked, form a nitrogen-containing saturated heterocycle having 4 to 8 ring atoms which is unsubstituted or substituted by C1-C6 alkyl, C1-C6 alkoxy or halogen, the nitrogen-containing saturated heterocycle is piperidine ring, a morpholine ring, a piperazine ring, an N-methylpiperazine ring, a homomorpholine ring, or a homopiperazine ring; and $R_3$ is

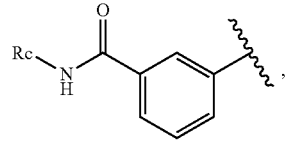

, wherein Rc is H or C1-C3 alkyl.

2. The compound of claim 1, or the isomer, the pharmaceutically acceptable salt, the ester or the solvate thereof, wherein, $R_1$ and $R_2$ are each independently 3-oxa-8-azabicyclo[3.2.1]octanyl, 8-oxa-3-azabicyclo[3.2.1]octanyl, or $NR_AR_B$, and at least one of $R_1$ and $R_2$ is 3-oxa-8-azabicyclo[3.2.1]octanyl or 8-oxa-3-azabicyclo[3.2.1]octanyl;

wherein $R_A$ and $R_B$ are each independently H, C1-C3 alkyl unsubstituted or substituted by C1-C3 alkoxy or halogen, or C1-C3 alkoxy unsubstituted or substituted by halogen, or $R_A$ and $R_B$, together with N to which they are linked, form a nitrogen-containing saturated heterocycle having 6 to 7 ring atoms which is unsubstituted or substituted by C1-C3 alkyl, C1-C3 alkoxy or halogen.

3. The compound of claim 1, or the isomer, the pharmaceutically acceptable salt, the ester or the solvate thereof, wherein $R_1$ and $R_2$ are each independently 3-oxa-8-azabicyclo[3.2.1]octanyl, 8-oxa-3-azabicyclo[3.2.1]octanyl, or $NR_AR_B$, and at least one of $R_1$ and $R_2$ is 3-oxa-8-azabicyclo[3.2.1]octanyl or 8-oxa-3-azabicyclo[3.2.1]octanyl;

wherein $R_A$ and $R_B$, together with N to which they are linked, form a morpholine ring unsubstituted or substituted by C1-C3 alkyl, C1-C3 alkoxy or halogen.

4. The compound of claim 1, or the isomer, the pharmaceutically acceptable salt, the ester or the solvate thereof according to claim 1, wherein $R_1$ is

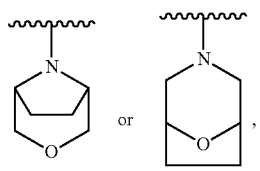 [SMILES: *N1C2CCC1COC2 ; *N1CC2CCC(C1)O2]

$R_2$ is

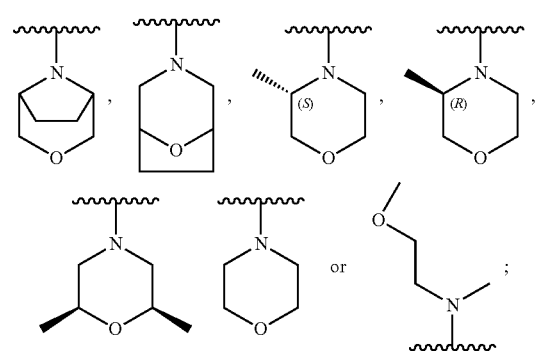

or, $R_2$ is

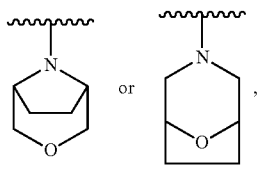

$R_1$ is

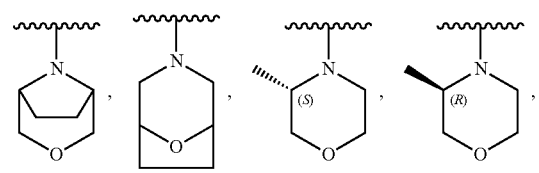

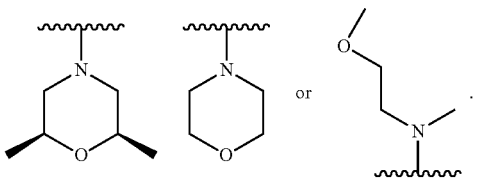

5. The compound of claim 1, or the isomer, the pharmaceutical acceptable salt, the ester or the solvate thereof, wherein Rc is H or methyl.

6. The compound of claim 1, or the isomer, the pharmaceutical acceptable salt, the ester or the solvate thereof, wherein the compound represented by formula (Ia) is selected from the group consisting of:

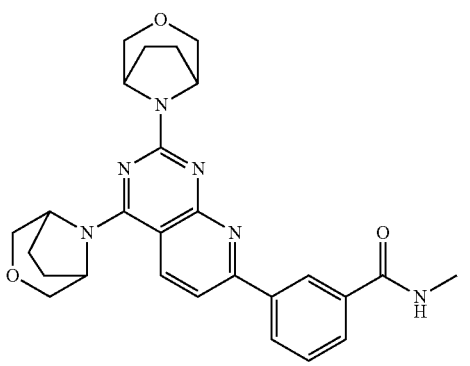

35

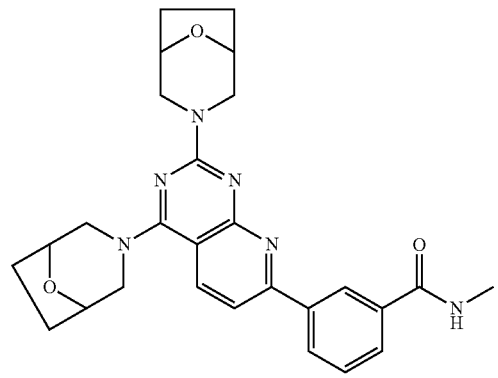

36

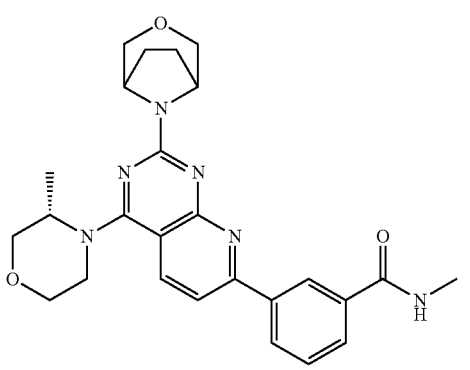

37

| 38 | 42 |
|---|---|
| 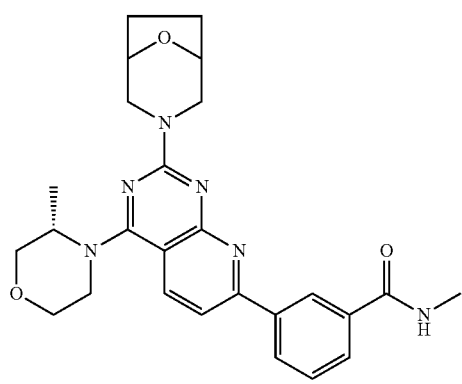 | 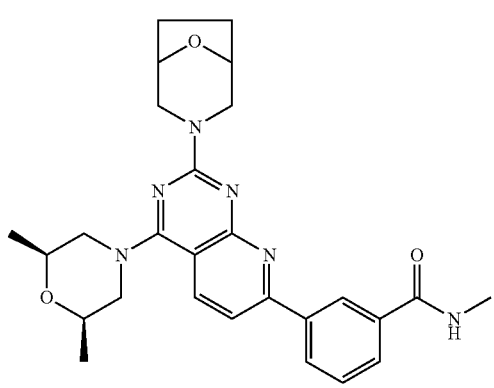 |
| 39 | 43 |
| 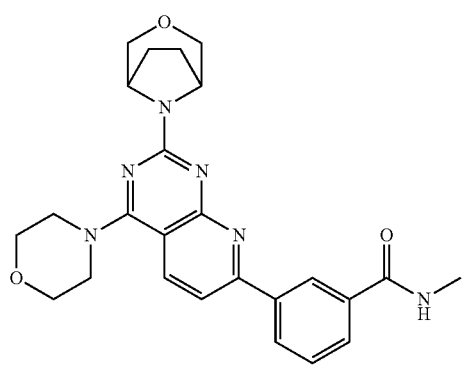 | 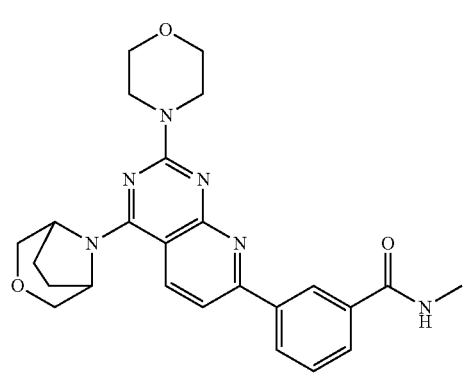 |
| 40 | 44 |
| 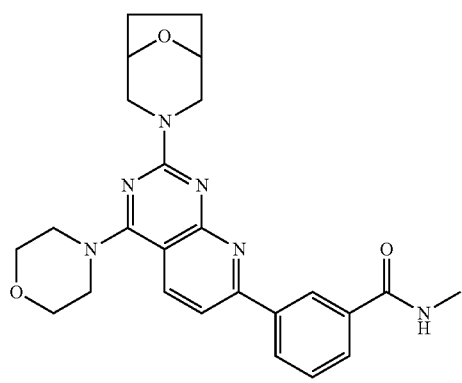 | 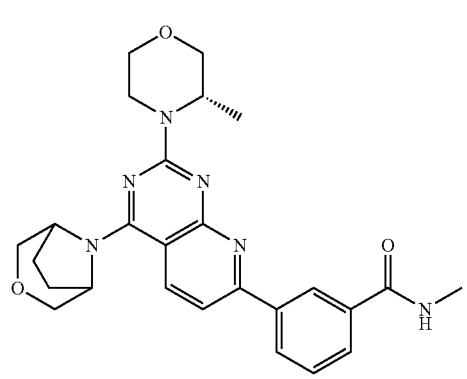 |
| 41 | 45 |
| 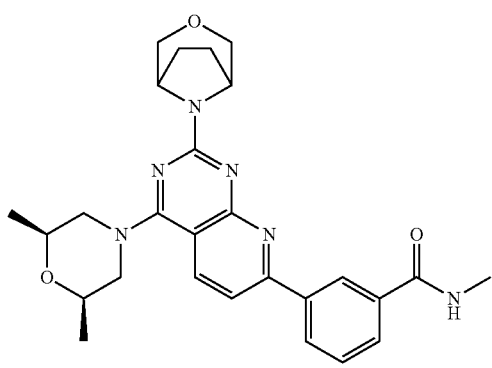 | 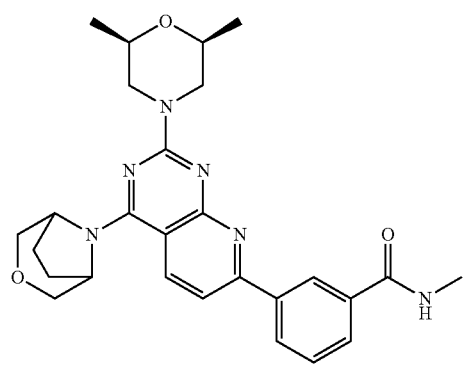 |

46 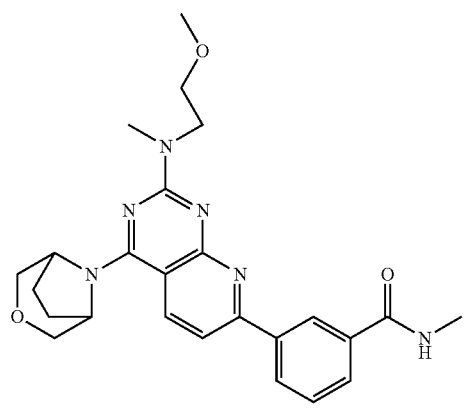

47 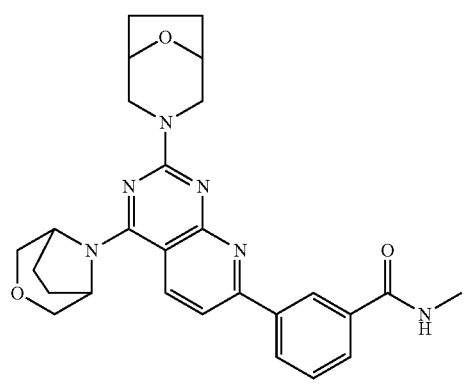

48 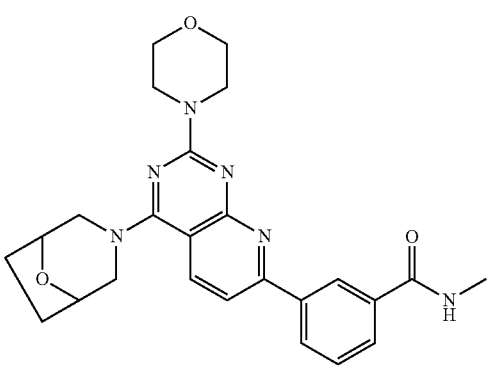

49 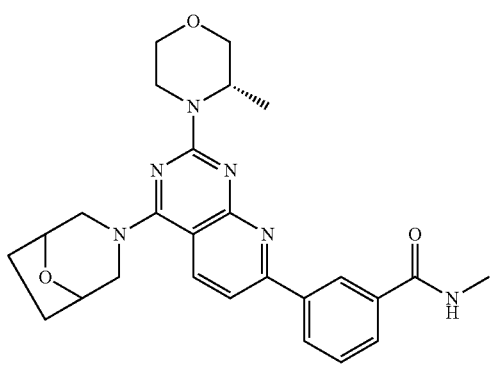

50 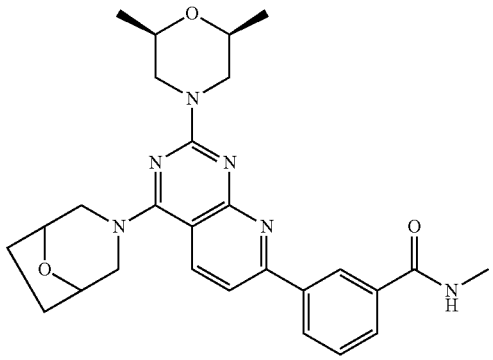

51 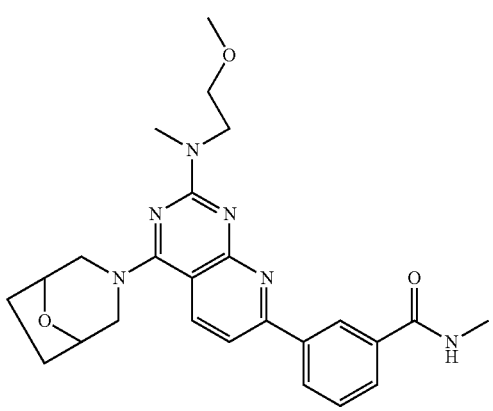

52 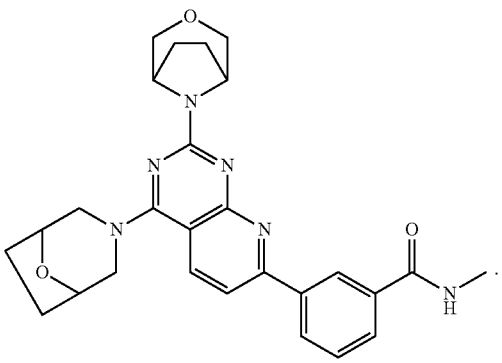

7. A pharmaceutical composition comprising a therapeutically effective amount of the compound of claim 1, or the isomer, the pharmaceutical acceptable salt, the ester or the solvate thereof, and optionally, a pharmaceutically acceptable carrier or excipient.

8. The compound of claim 1, or the isomer, the pharmaceutically acceptable salt, the ester or the solvate thereof, wherein
$R_1$ is

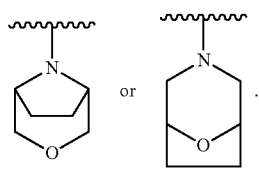

9. The compound of claim 1, or the isomer, the pharmaceutically acceptable salt, the ester or the solvate thereof, wherein
$R_2$ is
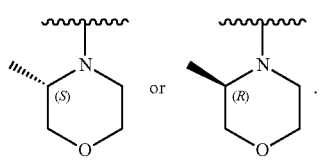
10. The compound of claim 1, selected from the group consisting of
35
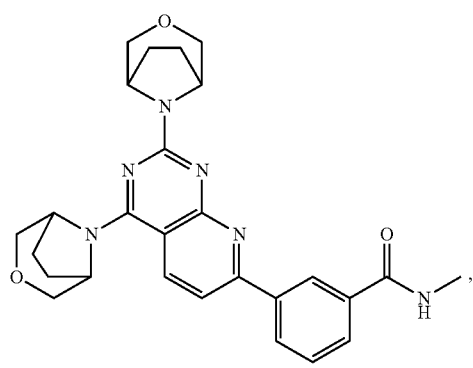
37
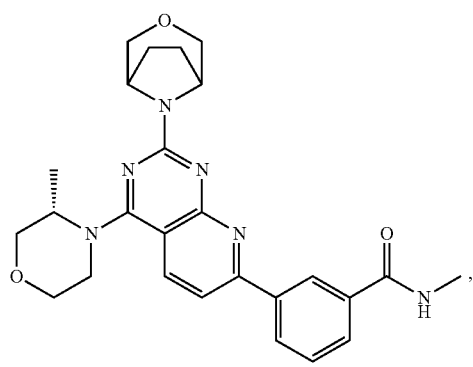
38
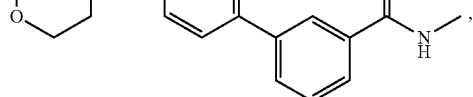
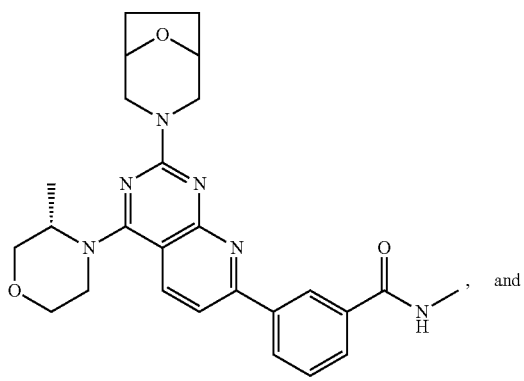, and
44
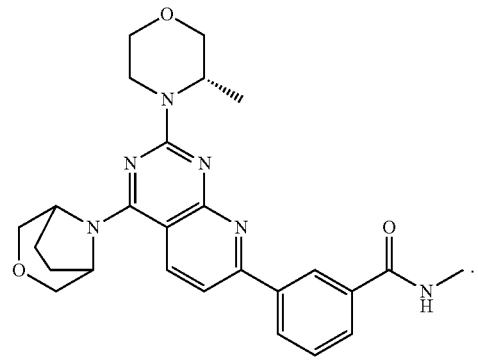
11. The pharmaceutical composition of claim 7, wherein the compound of claim 1 is selected from the group consisting of
35
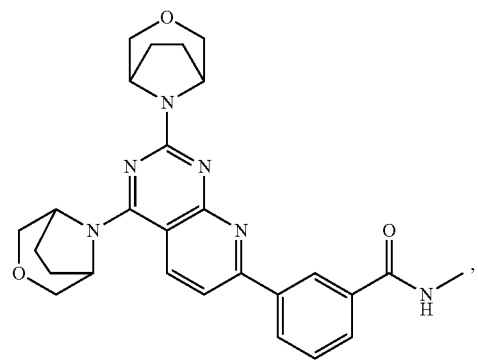
37
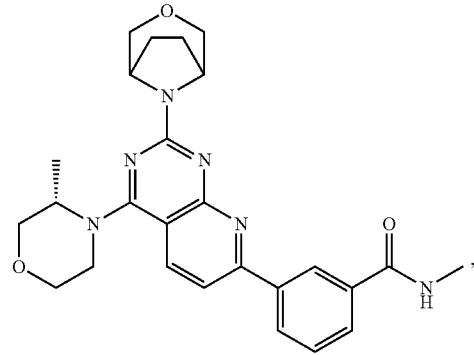
38
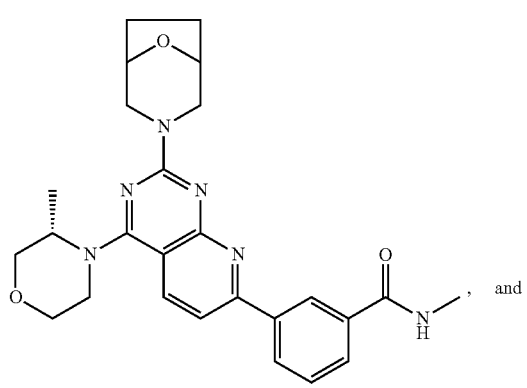, and

44

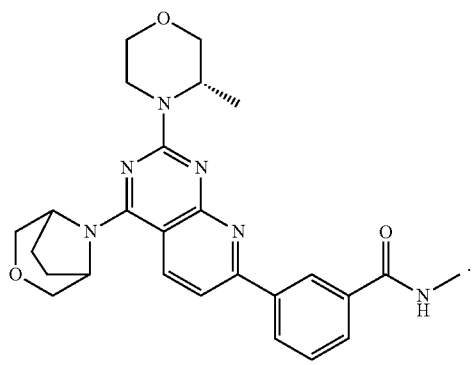

12. A method for treating a disease or condition in a patient in need thereof comprising administering to the patient a therapeutically effective amount of a compound of claim 1, or the isomer, the pharmaceutically acceptable salt, the ester or the solvate thereof, wherein the disease or condition is caused by dysfunction of PI3K-AKT-mTOR signaling pathway, wherein the disease or condition is selected from the group consisting of:

liver cancer, non-small cell lung cancer, skin cancer, colon cancer, breast cancer, brain cancer, kidney cancer, prostate cancer, and pancreatic cancer.

13. The method of claim 12, wherein the compound of claim 1 is selected from the group consisting of

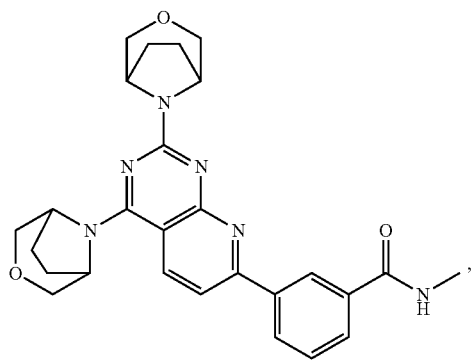

37

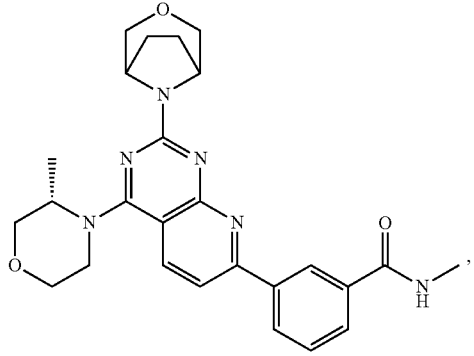

38

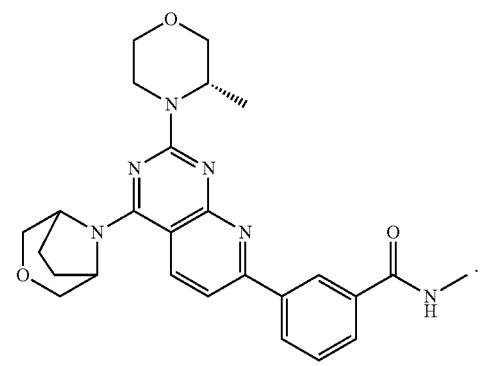

, and

44

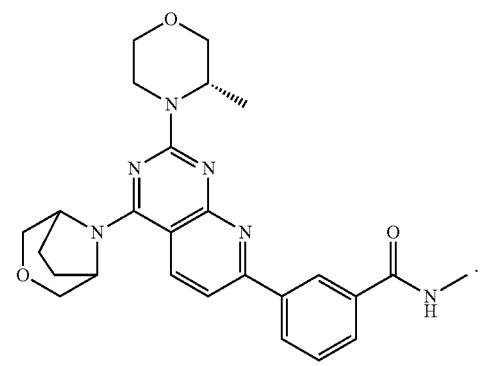

.

* * * * *